US010293041B2

(12) United States Patent
Brey et al.

(10) Patent No.: US 10,293,041 B2
(45) Date of Patent: *May 21, 2019

(54) MULTIVALENT STABLE VACCINE COMPOSITION AND METHODS OF MAKING SAME

(71) Applicant: Soligenix, Inc., Princeton, NJ (US)

(72) Inventors: Robert Brey, Grayslake, IL (US); Christopher Schaber, Princeton, NJ (US)

(73) Assignee: Soligenix, Inc., Princeton, NJ (US)

( * ) Notice: Subject to any disclaimer, the term of this patent is extended or adjusted under 35 U.S.C. 154(b) by 14 days.

This patent is subject to a terminal disclaimer.

(21) Appl. No.: 14/795,872

(22) Filed: Jul. 9, 2015

(65) Prior Publication Data

US 2017/0007682 A1 Jan. 12, 2017

US 2017/0333544 A9 Nov. 23, 2017

Related U.S. Application Data

(60) Provisional application No. 62/022,353, filed on Jul. 9, 2014.

(51) Int. Cl.

| | |
|---|---|
| ***A61K 39/07*** | (2006.01) |
| ***A61K 39/02*** | (2006.01) |
| ***A61K 39/39*** | (2006.01) |
| ***C07K 16/12*** | (2006.01) |
| ***A61K 39/00*** | (2006.01) |

(52) U.S. Cl.

CPC .............. *A61K 39/07* (2013.01); *A61K 39/00* (2013.01); *A61K 39/02* (2013.01); *A61K 39/39* (2013.01); *C07K 16/1278* (2013.01); *A61K 2039/55505* (2013.01); *A61K 2039/55511* (2013.01); *A61K 2039/55572* (2013.01); *A61K 2039/70* (2013.01); *C07K 2317/76* (2013.01)

(58) Field of Classification Search

None

See application file for complete search history.

(56) References Cited

U.S. PATENT DOCUMENTS

| | | | | |
|---|---|---|---|---|
| 7,998,487 B2 * | 8/2011 | Young | A61K 39/07 424/196.11 |
| 8,808,710 B2 * | 8/2014 | Randolph | A61K 39/08 424/234.1 |
| 2013/0280293 A1 | 10/2013 | Kuppuswamy et al. | |
| 2013/0309273 A1 * | 11/2013 | Hassett | A61K 9/19 424/400 |

OTHER PUBLICATIONS

Vance et al. 2015 (Combination of Two Candidate Subunit Antigens Elicits Protective Immunity to Ricin and Anthrax Toxin in Mice; Vaccine 33(3):417-421).*

Hassett et al. 2015 (Glassy-State Stabilization of a Dominant Negative Inhibitor Anthrax Vaccine Containing Aluminum Hydroxide and Glycopyranoside Lipid A Adjuvants; Pharmaceutical Biotechnology 104: 627-639).*

Mbow et al. 2010 (New adjuvants for human vaccines; Current Opinion in Immunology 22:411-416).*

Coler et al. 2011 (Development and Characterization of Synthetic Glucopyranosyl Lipid Adjuvant System as a Vaccine Adjuvant; PLoS ONE 6(1): e16333. doi:10.1371/journal.pone.0016333).*

Clapp et al. 2011 (Vaccines with Aluminum containing Adjuvants: Optimizing Vaccine Efficiency and Thermal Stability; Journal of Pharmaceutical Sciences 100: 388-401) (Year: 2011).*

Coler et al. 2011 (PLoS ONE 6(1): e16333.doi: 10.1371/ journal.pone.0016333 (Year: 2011).*

Schaber et al. Soligenix, Inc., Annual Report on Form 10-K, Mar. 26, 2014.

* cited by examiner

*Primary Examiner* — Mary Maille Lyons

(74) *Attorney, Agent, or Firm* — Lewis Kohn & Walker LLP; David M. Kohn; Kari Moyer-Henry

(57) ABSTRACT

Stable immunogenic composition capable of eliciting a robust and durable immune response yielding a measurable increase in neutralizing antibodies at least 200 days post-administration, comprising at least one antigen consisting of a ribosome inactivating protein and at least one antigen comprising a toxin derived from bacterial spores. Method making and using a stable immunogenic composition capable of eliciting a stable immune response yielding a measurable increase in neutralizing antibodies at least 200 days post-administration, comprising providing an immunogenic composition comprising at least one antigen comprising a ribosome inactivating protein and at least one antigen comprising a toxin derived from bacterial spores and administering the immunogenic composition to an individual.

16 Claims, 6 Drawing Sheets

Specification includes a Sequence Listing.

A.

B.

SEQUENCE LISTING

```
<160> NUMBER OF SEQ ID NOS: 1

<210> SEQ ID NO 1
<211> LENGTH: 745
<212> TYPE: PRT
<213> ORGANISM: Artificial Sequence
<220> FEATURE:
<223> OTHER INFORMATION: Immunological peptide

<400> SEQUENCE: 1

Met Asp Ile Gly Ile Asn Ser Asp Pro Met Glu Val Lys Gln Glu Asn
1               5                   10                  15

Arg Leu Leu Asn Glu Ser Glu Ser Ser Ser Gln Gly Leu Leu Gly Tyr
            20                  25                  30

Tyr Phe Ser Asp Leu Asn Phe Gln Ala Pro Met Val Val Thr Ser Ser
        35                  40                  45

Thr Thr Gly Asp Leu Ser Ile Pro Ser Ser Glu Leu Glu Asn Ile Pro
    50                  55                  60

Ser Glu Asn Gln Tyr Phe Gln Ser Ala Ile Trp Ser Gly Phe Ile Lys
65                  70                  75                  80

Val Lys Lys Ser Asp Glu Tyr Thr Phe Ala Thr Ser Ala Asp Asn His
                85                  90                  95

Val Thr Met Trp Val Asp Asp Gln Glu Val Ile Asn Lys Ala Ser Asn
            100                 105                 110

Ser Asn Lys Ile Arg Leu Glu Lys Gly Arg Leu Tyr Gln Ile Lys Ile
        115                 120                 125

Gln Tyr Gln Arg Glu Asn Pro Thr Glu Lys Gly Leu Asp Phe Lys Leu
    130                 135                 140

Tyr Trp Thr Asp Ser Gln Asn Lys Lys Glu Val Ile Ser Ser Asp Asn
145                 150                 155                 160

Leu Gln Leu Pro Glu Leu Lys Gln Lys Ser Ser Asn Ser Arg Lys Lys
                165                 170                 175

Arg Ser Thr Ser Ala Gly Pro Thr Val Pro Asp Arg Asp Asn Asp Gly
            180                 185                 190

Ile Pro Asp Ser Leu Glu Val Glu Gly Tyr Thr Val Asp Val Lys Asn
        195                 200                 205

Lys Arg Thr Phe Leu Ser Pro Trp Ile Ser Asn Ile His Glu Lys Lys
    210                 215                 220

Gly Leu Thr Lys Tyr Lys Ser Ser Pro Glu Lys Trp Ser Thr Ala Ser
225                 230                 235                 240

Asp Pro Tyr Ser Asp Phe Glu Lys Val Thr Gly Arg Ile Asp Lys Asn
                245                 250                 255

Val Ser Pro Glu Ala Arg His Pro Leu Val Ala Ala Tyr Pro Ile Val
            260                 265                 270

His Val Asp Met Glu Asn Ile Ile Leu Ser Lys Asn Glu Asp Gln Ser
        275                 280                 285

Thr Gln Asn Thr Asp Ser Gln Thr Arg Thr Ile Ser Lys Asn Thr Ser
    290                 295                 300

Thr Ser Arg Thr His Thr Ser Glu Val His Gly Asn Ala Glu Val His
305                 310                 315                 320

Ala Ser Phe Phe Asp Ile Gly Gly Ser Val Ser Ala Gly Phe Ser Asn
                325                 330                 335

Ser Asn Ser Ser Thr Val Ala Ile Asp His Ser Leu Ser Leu Ala Gly
            340                 345                 350

Glu Arg Thr Trp Ala Glu Thr Met Gly Leu Asn Thr Ala Asp Thr Ala
```

-continued

```
        355                 360                 365

Arg Leu Asn Ala Asn Ile Arg Tyr Val Asn Thr Gly Thr Ala Pro Ile
    370                 375                 380

Tyr Asn Val Leu Pro Thr Thr Ser Leu Val Leu Gly Lys Asn Gln Thr
385                 390                 395                 400

Leu Ala Thr Ile Lys Ala Asp Glu Asn Gln Leu Ser Gln Ile Leu Ala
                405                 410                 415

Pro Asn Asn Tyr Tyr Pro Ser Lys Asn Leu Ala Pro Ile Ala Leu Asn
            420                 425                 430

Ala Gln Lys Asp Phe Ser Ser Thr Pro Ile Thr Met Asn Tyr Asn Gln
        435                 440                 445

Phe Leu Glu Leu Glu Lys Thr Lys Gln Leu Arg Leu Asp Thr Asp Gln
    450                 455                 460

Val Tyr Gly Asn Ile Ala Thr Tyr Asn Phe Glu Asn Gly Arg Val Arg
465                 470                 475                 480

Val Asp Thr Gly Ser Asn Trp Ser Glu Val Leu Pro Gln Ile Gln Glu
                485                 490                 495

Thr Thr Ala Arg Ile Ile Phe Asn Gly Lys Asp Leu Asn Leu Val Glu
            500                 505                 510

Arg Arg Ile Ala Ala Val Asn Pro Ser Asp Pro Leu Glu Thr Thr Lys
        515                 520                 525

Pro Asp Met Thr Leu Lys Glu Ala Leu Lys Ile Ala Phe Gly Phe Asn
    530                 535                 540

Glu Pro Asn Gly Asn Leu Gln Tyr Gln Gly Lys Asp Ile Thr Glu Phe
545                 550                 555                 560

Asp Phe Asn Phe Asp Gln Gln Thr Ser Gln Asn Ile Lys Asn Gln Leu
                565                 570                 575

Ala Glu Leu Asn Ala Thr Asn Ile Tyr Thr Val Leu Asp Lys Ile Lys
            580                 585                 590

Leu Asn Ala Lys Met Asn Ile Leu Ile Arg Asp Lys Arg Phe His Tyr
        595                 600                 605

Asp Arg Asn Asn Ile Ala Val Gly Ala Asp Glu Ser Val Val Lys Glu
    610                 615                 620

Ala His Arg Glu Val Ile Asn Ser Ser Thr Glu Gly Leu Leu Leu Asn
625                 630                 635                 640

Ile Asp Lys Asp Ile Arg Lys Ile Leu Ser Gly Tyr Ile Val Glu Ile
                645                 650                 655

Glu Asp Thr Glu Gly Leu Lys Glu Val Ile Asn Asp Arg Tyr Asp Met
            660                 665                 670

Leu Asn Ile Ser Ser Leu Arg Gln Asp Gly Lys Thr Phe Ile Asp Phe
        675                 680                 685

Lys Lys Tyr Asn Asp Lys Leu Pro Leu Tyr Ile Ser Asn Pro Asn Tyr
    690                 695                 700

Lys Val Asn Val Tyr Ala Val Thr Lys Glu Asn Thr Ile Ile Asn Pro
705                 710                 715                 720

Ser Glu Asn Gly Asp Thr Ser Thr Asn Gly Ile Lys Lys Ile Leu Ile
                725                 730                 735

Phe Ser Lys Lys Gly Tyr Glu Ile Gly
            740                 745
```

MULTIVALENT STABLE VACCINE COMPOSITION AND METHODS OF MAKING SAME

RELATED APPLICATIONS

This application claims priority from U.S. Provisional Application No. 62/022,353, filed on Jul. 9, 2014, the contents of which are hereby incorporated by reference herein.

FIELD OF THE INVENTION

The invention relates to stable immunogenic compositions comprising more than one antigen and conferring increased immunity to an individual. The invention also related to methods of making and using the stable immunogenic compositions described herein.

BACKGROUND OF THE INVENTION

Vaccination is an important tool for handling health care programs both in developed and developing nations. The number of recommended vaccines has increased significantly in recent years against individual infections. Presently, the schedule of infants and children may require more than 24-25 separate shots of vaccines for effective immunization against life threatening diseases.

The majority of vaccines currently in development belong to a specific class of subunit vaccine compositions, which consist of recombinant or purified pathogen-specific proteins or encoded antigens (from DNA) that will be expressed and presented in vivo in order to accomplish or elicit the desired immunogenic response. This type of vaccine presents an antigen to the immune system without introducing viral particles, whole or otherwise. While evidence suggests that live, attenuated pathogens and viral vectors can induce protective effects, they often cause unwanted side effects or raise safety concerns, which is one reason why subunit vaccines have risen to prominence in the field (Arvin et al., "New viral vaccines", *Virology,* 344:240-249 (2006); Yang et al., "A novel peptide isolated from phage library to substitute a complex system for a vaccine against staphylococci infection", *Vaccine,* 24:1117-1123 (2006)).

A combination vaccine which can provide immunogenicity against large number of diseases is always advantageous over the monovalent vaccines. We cannot reduce the number of immunizations required in infants and children to protect them from various fatal diseases but the compliance can be increased by reducing the number of separate vaccinations. A combination vaccine is advantageous over monovalent vaccine as it not only increases the compliance but it is also cost effective and convenient thereby reducing the chances of missing any vaccination. However, due to complications associated with the preparation of such combination vaccines due to possible interaction between the antigens has always been a challenge before the scientific community. Complications include immune interference when vaccine antigens are administered concurrently at the same site in the body, and instability of the antigens together in combinations, impeding the simultaneous development of protective immunity.

Combination vaccines, while greatly desired for ease of administration and increased compliance, pose difficulties in development due to factors including: physical and biochemical incompatibility between antigens and other components, immunological interference and stability. For instance, adjuvants (e.g. aluminum salt, oil-in-water emulsions) that modify the effects of other agents, such as a drug or vaccines, have few if any direct effects when administered alone. Adjuvants are often included in vaccines to enhance a recipient's immune response to a supplied antigen, while keeping the injected foreign material to a minimum. In a combination vaccine, a specific adjuvant may reduce the activity of one antigen and excessively increase the reactivity of another antigen. Buffers used to minimize changes in acidity of a solution (when an acid or base is added) may also interact with other vaccine components. Stabilizers are used to ensure vaccines maintain effectiveness during storage by counteracting the effects of temperature, pH and preservatives. Vaccine stability is essential, particularly where the cold chain is unreliable. However, stabilizers may also have an effect on other agents present in the vaccine. All these potential interactions between vaccine components can negatively effective vaccine potency reducing the immunogenicity of the vaccine.

The trend towards combination vaccines has the advantage of reducing discomfort to the recipient, facilitating scheduling, and ensuring completion of regiment. However, there is also the concomitant risk of reducing the vaccine's efficacy. It would be, therefore, advantageous to make vaccine combinations which meet the needs of a population, and which, in addition, do not interfere with each other. It would be of further advantage if the combination of the vaccines results in synergy with resulting improvement of one or both vaccines' efficacy, or improved correlates of protections for one or both vaccines.

An immune response is generated to an antigen through the interaction of the antigen with the cells of the immune system. The resultant immune response may be broadly distinguished into two extreme categories, being humoral or cell mediated immune responses (traditionally characterized by antibody and cellular effector mechanisms of protection, respectively). These categories of response have been termed Th2-type immune responses (humoral response) and Th1-type responses (cell-mediated response).

Extreme Th1-type immune responses may be characterized by the generation of antigen specific, haplotype-restricted cytotoxic T lymphocytes, and natural killer cell responses. In mice, Th1-type responses are often characterized by the generation of antibodies of the IgG2a subtype, while in the human these correspond to IgG1 type antibodies. Th2-type immune responses, on the other hand, are characterized by the generation of a broad range of immunoglobulin isotypes, including (in mice) IgG1, IgA, and IgM.

It can be considered that the driving force behind the development of these two types of immune responses are cytokines, a number of identified protein messengers which serve to help the cells of the immune system and steer the eventual immune response to either a Th1 or Th2 response. Thus, high levels of Th1-type cytokines tend to favor the induction of cell mediated immune responses to the given antigen, while high levels of Th2-type cytokines tend to result in the induction of humoral immune responses to the antigen.

It is known that certain vaccine adjuvants are particularly suited to the stimulation of either Th1- or Th2-type cytokine responses. Traditionally the best indicators of the Th1:Th2 balance of the immune response after a vaccination or infection includes direct measurement of the production of Th1 or Th2 cytokines by T lymphocytes in vitro after re-stimulation with antigen, and/or the measurement of the IgG1:IgG2a ratio of antigen specific antibody responses.

Thus, a Th1-type adjuvant is one which stimulates isolated T-cell populations to produce high levels of Th1-type cytokines when re-stimulated with antigen in vitro, and induces antigen specific immunoglobulin responses associated with Th1-type isotype. Suitable adjuvant systems which promote a predominantly Th1 response include Monophosphoryl lipid A or a derivative thereof, particularly 3-de-O-acylated monophosphoryl lipid A, and a combination of monophosphoryl lipid A, preferably 3-de-O-acylated monophosphoryl lipid A (3D-MPL) together with an aluminum salt.

Adjuvants are molecules, compounds, or macromolecular complexes that boost the potency and longevity of specific immune response to antigens, but cause minimal toxicity or long-lasting immune effects on their own. Adjuvants can be used to enhance immunogenicity, modulate the type of immune response, reduce the amount of antigen or the number of immunizations required, and improve the efficacy of vaccines in newborns or elderly. To be maximally effective, adjuvants must be selected judiciously and formulated appropriately based on the desired immune response. However, the number of adjuvants with acceptable efficacy and safety profiles is limited, and these proprietary molecules/compounds are in the hands of a few companies, as is most of the formulation expertise.

Vaccines containing recombinant proteins require an adjuvant to elicit a durable immune response (Callahan, Shorter, et al., 1991, The importance of surface charge in the optimization of antigen-adjuvant interactions, *Pharm Res*, v 8:851-8). The default position in developing subunit protein immunogens for human vaccines is to utilize aluminum adjuvants as the starting point. The use of aluminum adjuvants is thus fostered by the fact that the record of safety of newer formulations cannot match the long term acceptability of aluminum adjuvants in human vaccines. Overall, this has amounted to a lack of advanced adjuvants that can be applied to vaccine development, coupled with the fact that several of the most advanced adjuvant formulations/compounds are the property of large pharmaceutical companies. Aluminum-salt adjuvants are currently the most widely used adjuvants for general use in humans. Aluminum adjuvants are considered relatively weak, effective in generation of neutralizing antibodies against certain bacterial antigens, but relatively ineffective at inducing cellular immune responses. There is some consensus that the more effective vaccines with aluminum are those in which antigen is bound to the aluminum surface, rather than free in solution (Lindblad, 2004, Aluminium adjuvants—in retrospect and prospect, *Vaccine,* v 22:3658-68). For reproducibility of formulations and stability, it is desirable to define conditions for optimal binding of antigen to crystal surfaces, and conditions in which antigen does not desorb over time or under elevated stress conditions. To construct aluminum vaccines, it is necessary to carry out studies to optimize binding and desorption. Aluminum adjuvants have a point of zero charge (PZC) at a certain solution pH, but are charged at pHs above or below this value (White and Hem, 2000, Characterization of aluminium-containing adjuvants, *Dev Biol* (*Basel*), v 103:217-28). Selecting an optimal formulation pH is further complicated for a recombinant protein vaccine for which binding to aluminum salt adjuvants is generally required to obtain the desired immune response (McInerney, Brennan, et al., 1999, Analysis of the ability of five adjuvants to enhance immune responses to a chimeric plant virus displaying an HIV-1 peptide, *Vaccine*, v 17:1359-68). To facilitate protein binding to adjuvant, a solution pH is selected in which the protein and adjuvant have opposite charges. However, a solution pH that provides optimal protein stability, may not allow for appropriate binding of the vaccine to adjuvants. In such a scenario, a vaccine protein may have to be prepared at pH that is suboptimal for stability and lyophilized with appropriate stabilizing excipients to minimize degradation during long-term storage.

The emerging trend in these fields has been that it is not sufficient to engineer the protein target itself, but that potent, safe, adjuvant formulations must be utilized as an intrinsic component of vaccine design, from the earliest feasibility experiments through clinical testing. The use of formulation technology can result in a significant decrease in dose levels and number of vaccinations, an increase in the quality and breadth of the immune response, as well as long-term, sustained responses to the antigenic target. Adjuvant formulations consist of aqueous suspensions of vaccine particles, adsorption of antigens to salts of aluminum, oil-in-water emulsions of antigens, and nanovesicles such as liposomes or niosomes.

In the case of aluminum adjuvants, it has been suggested that to provide adequate immunogenicity, antigens must be adsorbed on the surface of the adjuvant. (Gupta et al., 1995, Adjuvant Properties of Aluminum and Calcium Compounds, *Pharmaceutical Biotechnology,* 6: 229-248; and White and Hem, 2000, Characterization of aluminum-containing adjuvants, *Dev Biol* (*Basel*), 103: 217-28). This adsorption is typically facilitated through electrostatic interactions between the antigen and adjuvant, and the formulation pH is usually chosen so that the antigen and adjuvant are oppositely charged (Callahan et al. 1991). The surface charge on the adjuvant also can be modified by surface exchange reactions with buffer salts such as phosphate, succinate, and citrate (Hem and White, 1984, Characterization of aluminum hydroxide for use as an adjuvant in parenteral vaccines. *J Parenter Sci Technol,* 38(1): p. 2-10; Chang et al., 1997, Role of the electrostatic attractive force in the adsorption of proteins by aluminum hydroxide adjuvant. PDA *J Pharm Sci Technol,* 51(1): p. 25-9; and Rinella et al., 1996, Treatment of aluminium hydroxide adjuvant to optimize the adsorption of basic proteins. *Vaccine,* 14(4): p. 298-300.)

The mechanisms of action of aluminum-salt adjuvants are poorly understood, but are likely due to several different mechanisms. (Lindblad 2004. "Aluminium compounds for use in vaccines" Immunol. *Cell Biol,* 82(5):497-505; Gupta and Siber, 1995, Adjuvants for Human Vaccines—Current Status, Problems and Future-Prospects. *Vaccine* 13(14): 1263-1276; Gupta and Rost, 2000, Aluminum Compounds as Vaccine Adjuvants, In O'Hagan D, editor *Vaccine Adjuvants: Preparation Methods and Research Protocols*, ed., Totowa, N.J.: Humana Press Inc. p 65-89; Cox and Coulter, 1997, Adjuvants—a classification and review of their modes of action, *Vaccine* 15(3):248-256). Common proposed mechanisms are that the adjuvant acts as a depot at the site of injection, wherein the antigen is slowly released after administration. (Cox and Coulter, 1997)).

Another proposed mechanism is that the adjuvant aids in delivery of the antigen to antigen-presenting cells (Lindblad 2004). A further proposed mechanism is that adjuvant serves as an immunostimulator and elicits Th2 cytokines (Grun and Maurer 1989, Different T helper cell subsets elicited in mice utilizing two different adjuvant vehicles: the role of endogenous interleukin 1 in proliferative responses, *Cell Immunol,* 121(1):134-145)). Yet another proposed mechanism is that the presence of an adjuvant destabilizes protein antigens on the surface of the adjuvant making them more susceptible to proteolytic degradation (Jones et al., 2005, Effects of adsorption to aluminum salt adjuvants on the structure and stability of model protein antigens. *J Biol Chem* 280(14):13406-13414; and That et al., 2004. "Antigen stability controls antigen presentation" *J Biol Chem,* 279(48):50257-50266)).

Although the mechanism of action is not fully understood, it is likely that surface area, surface charge, and morphology of the adjuvant are important factors dictating the immune response to antigens adsorbed onto these adjuvants (Hem and White 1984). It is generally theorized that the smaller the particle size of the vaccine adjuvant, the more immunogenic the vaccine preparation, especially when particle size is approximately 1 micron, a size best suited for uptake into professional antigen presenting cells (Maa et al., 2003. Stabilization of alum-adjuvanted vaccine dry powder formulations: mechanism and application. *J Pharm Sci* 92(2): 319-332, Diminsky et al., 1999. Physical, chemical and immunological stability of CHO-derived hepatitis B surface antigen (HBsAg) particles. *Vaccine* 18(1-2):3-17).

Aluminum-salt adjuvants provide a well explored means to augment the immunogenicity of protein or peptide subunit vaccines. However, a variety of exploratory formulations to enhance vaccines have been developed as more potent alternative to aluminum-salts adjuvants, but are not currently available in FDA-licensed human vaccines. Formulations designed to enhance immune responses include a variety of compositions based on water-in-oil emulsions, oil-in-water emulsions, self-assembling macrostructures, cytokines, saponins, toll-like receptor agonists (TLR-4, TLR-5, and TLR-9), immunostimulatory double stranded RNA species, unmethylated DNA oligonucleotides, and polymeric microparticles and nanostructures. Many of these compositions are directed towards improving the immunogenicity of injected vaccines, and some variations can be applied to altering routes of delivery for intranasal or oral vaccination.

As an example of one class of immunostimulatory molecules that can be used to enhance vaccine immunogenicity, bacterial DNA, but not vertebrate DNA, can be used because of direct immunostimulatory effects that activate lymphocytes. This is due to unmethylated CpG dinucleotides being present at the expected frequency in bacterial DNA but are under-represented and methylated in vertebrate DNA (Krieg et al., 1995). Activation may also be triggered by addition of synthetic oligodeoxynucleotides (ODN) that contain an unmethylated CpG dinucleotide in a particular sequence context. CpG DNA induces proliferation of almost all (>95%) B cells and increases immunoglobulin (Ig) secretion. This B cell activation by CpG DNA is T cell independent and antigen non-specific. However, B cell activation by low concentrations of CpG DNA has strong synergy with signals delivered through the B cell antigen receptor for both B cell proliferation and Ig secretion (Krieg et al., 1995). This strong synergy between the B cell signaling pathways triggered through the B cell antigen receptor and by CpG DNA promotes antigen specific immune responses.

In addition to its direct effects on B cells, CpG DNA also directly activates monocytes, macrophages, and dendritic cells to secrete a variety of cytokines, including high levels of IL-12 (Klinman et al., 1996; Halpern et al., 1996; Cowdery et al., 1996). These cytokines stimulate natural killer (NK) cells to secrete gamma-interferon (IFN.gamma.) and have increased lytic activity (Klinman et al., 1996, supra; Cowdery et al., 1996, supra; Yamamoto et al., 1992; Ballas et al., 1996). Overall, CpG DNA induces a Th1-like pattern of cytokine production dominated by IL-12 and IFN-gamma with little secretion of Th2 cytokines (Klinman et al., 1996).

Other molecules stimulate toll like receptors. One example is flagellin, the protein subunit comprising numerous bacterial flagella. Flagellin is a TLR-5 ligand and triggers at least one of the biological functions of antigen presenting cells upon such binding. Flagella are found on the surface of rod and spiral shaped bacteria, including members of the genera *Escherichia, Salmonella, Proteus, Pseudomonas, Bacillus, Campylobacter, Vibrio, Treponema, Legionella*, Clostridia, and *Caulobacter*. The conserved regions of flagellins are important for TLRS binding, while the polymorphic central region can be deleted without affecting binding to TLRS. Flagellin sequences from numerous bacteria are available in the art, such as Genbank accession numbers D13689, YP.sub.-275549, YP.sub.-275550, AAU18718, AAU18717, ZP.sub.-00743095, EA052626, YP.sub.-315348, AAT28337, AAT28336, AAT28335, AAT28334, AAT28333, AAZ36356, AAZ33167, AAZ94424, AAZ91670, NP.sub.-414908, BAD18052, and BAD18051.

As a third example of purified adjuvant immune stimulants, nontoxic (chemically synthesized or enzymatically modified) derivatives of gram negative lipopolysaccharides are potent adjuvants and act by stimulating lymphocytes through TLR-4 binding and activation. For example, monophosphoryl lipid A (MPL) is a derivative of the lipid A component of lipopolysaccharide and is a potent activator of pro-inflammatory cytokines. Although native lipid A and its parent LPS have powerful pyrogenic properties and in humans induce febrile responses (Greisman and Homick, *J Immunol,* 109:1210-1215 (1972); Greisman and Homick, *J Infect Dis,* 128:257-263 (1973); Abernathy and Spink, *J Clin Invest,* 37:219-225 (1958); Rietschel et al, supra; and Raetz, supra (1993)), MPL and its chemically synthesized analogues are not toxic but induce a compendium of host proinflammatory cytokines including IL-1, IL-6, and TNF-alpha.

In addition, to enhance the immune response to subunits adsorbed to aluminum salts, it is likely that co-adjuvants will be required in order to generate effective antibody responses in humans after one or two doses. A number of adjuvant compounds that are compatible with aluminum salts have been evaluated as adjuvants in recent years. Primarily these adjuvants include Monophosphoryl Lipid A (MPL) and QS-21, and CpG sequences.

Recent data with anthrax vaccine indicates in human studies that AVA, an AlOH adsorbed vaccine, can be significantly enhanced by adding CpG 7909 to the adjuvant formulations in non-human primates and humans, in terms of total anti-rPA antibodies and anthrax toxin neutralizing antibodies, although no data describe the long term thermal stability of CpG-containing vaccines (Klinman, 2006, CpG oligonucleotides accelerate and boost the immune response elicited by AVA, the licensed anthrax vaccine, *Expert Rev Vaccines,* 5:365-9).

MPL and QS-21 have been also used with aluminum salts as well as in proprietary oil emulsion formulations being developed by Glaxo Smith Kline Biologics. QS-21 has been evaluated in AlOH vaccines in humans and animal models with good evidence of tolerability and systemic safety. QS-21 is thought to bind to aluminum salts through ionic and hydrophobic interactions, as well as some part of it remaining in solution (in aqueous vaccines) in a micellar form. QS-21 is a saponin purified from tree bark with broad adjuvant effects to induce both antibody and cell mediated immunity. Though the mechanism is not understood, dose levels effective in conjunction with human vaccines have been evaluated.

QS-21 with aluminum has been evaluated in clinical studies and independent safety studies of QS-21 formulated with antigens have been studied. QS-21 has been associated with stinging at the site of injection (that resolves), with very little evidence of systemic side effects (Waite, Jacobson et al., 2001, Three double-blind, randomized trials evaluating the safety and tolerance of different formulations of the saponin adjuvant QS-21, *Vaccine,* 19:3957-67). Several studies in humans have shown that QS-21 enhances responses to antigens that are adsorbed to aluminum. These include several trials in malaria vaccine candidates (Nardin, Oliveira et al., 2000, Synthetic malaria peptide vaccine elicits high levels of antibodies in vaccinees of defined HLA genotypes, *J Infect Dis,* 182:1486-96; Kashala, Amador et al., 2002, Safety, tolerability and immunogenicity of new formulations of the *Plasmodium falciparum* malaria peptide vaccine SPf66 combined with the immunological adjuvant QS-21, *Vaccine,* 20:2263-77), HIV gp120 (Evans, McElrath et al., 2001, QS-21 promotes an adjuvant effect allowing for reduced antigen dose during HIV-1 envelope subunit immunization in humans, *Vaccine,* 19:2080-91) and more recently Rhesus macaque trials of Dengue virus subunits in which neutralizing titers and protection were enhanced by QS-21 (Putnak, Coller et al., 2005, An evaluation of dengue type-2 inactivated, recombinant subunit, and live-attenuated vaccine candidates in the rhesus macaque model, *Vaccine,* 23:4442-52). The solution stability of QS-21 has been well studied under long term stability studies, and has shown that adjuvant active QS-21 (which actually consists of two isomeric forms) is highly stable in slightly acidic buffers for over 4 years, though less than 10 days at 40° C. (Kensil and Kammer, 1998, QS-21: a water-soluble triterpene glycoside adjuvant, *Expert Opin Investig Drugs,* 7:1475-82). QS-21 is stored as a dried powder and in that form is stable indefinitely.

Lyophilization of proteins to stabilize structure and activity for storage and reconstitution has been commonly applied to recombinant protein therapeutic proteins. This has been usually accomplished by freeze drying in the presence of disaccharides such as trehalose and other excipients that promote a glass state during process and storage. Proteins can be stored for long term as long as the product is stored below its glass transition temperature (Tg), above which the material transitions into a rubbery state. Excipients are thought to stabilize protein in the amorphous state through interactions of the stabilizer with specific sites substituting for water during drying and by simultaneously suppressing translational and rotational motions of the protein molecule (α-relaxations) or portions of the molecule (β-relaxations).

Drying technology has been less frequently applied to long term storage of vaccines, especially in the case of vaccines adsorbed to aluminum phosphate or aluminum hydroxide adjuvants. Very little data is available on the storage of dried vaccines under elevated temperature conditions, as most of the attempts to generate dried vaccines have been to obtain inhalable powders or preparations able to survive moderate excursions in temperature. For example, because the yellow fever vaccine is used primarily in tropical climates, lyophilization in the presence of stabilizers (lactose, sorbitol) has been used to preserve viability of the live virus vaccine (Monath, 1996, Stability of yellow fever vaccine, *Dev Biol Stand,* 87:219-25). Without excipients during lyophilization and storage, activity is rapidly lost above −20° C., but the stabilized vaccine can withstand more than two weeks at 37° C. A lyophilized dried vaccine for the cattle disease rinderpest has also been developed and can be employed for up to a month after leaving the cold chain in African field conditions (House and Mariner, 1996, Stabilization of rinderpest vaccine by modification of the lyophilization process, *Dev Biol Stand,* 87:235-44). Similar attempts to use variations on process and drying have been recently applied to measles vaccine development (Burger, Cape et al., 2008, Stabilizing formulations for inhalable powders of live-attenuated measles virus vaccine, *J Aerosol Med Pulm Drug Deliv,* 21:25-34; Burger, Cape et al., 2008, Stabilizing Formulations for Inhalable Powders of Live-Attenuated Measles Virus Vaccine, *J Aerosol Med*) and for dried vaccine powders for influenza where it is likely very important to devise conditions that permit retention of the structure of the immunogen (Amorij, Meulenaar et al., 2007, Rational design of an influenza subunit vaccine powder with sugar glass technology: preventing conformational changes of haemagglutinin during freezing and freeze-drying, *Vaccine,* 25:6447-57; Amorij, Huckriede et al., 2008, Development of Stable Influenza Vaccine Powder Formulations: Challenges and Possibilities, *Pharm Res*).

As a stabilizer, small amounts of formaldehyde are occasionally added to vaccines, including the current AVA anthrax vaccine (Biothrax®), and may act by cross-linking proteins forming more immunogenic protein aggregates on the surface of aluminum crystals (Little, Ivins et al., 2007, Effect of aluminum hydroxide adjuvant and formaldehyde in the formulation of rPA anthrax vaccine, *Vaccine,* 25:2771-7). Formaldehyde had been used historically as the stabilizer of choice in the older vaccines derived from culture supernatants, such as tetanus toxoid, botulinum toxoids, and others. The current AVA vaccine is labeled for 3 year stability, where stability is a function of a number of biochemical evaluations and potency. Although a moderate amount of stability can be achieved with liquid suspension vaccines, it is not likely that all stability parameters can be met for longer storage periods that are required for vaccines to be stockpiled and distributed.

Successful drying of therapeutic proteins, while retaining structure and function, is dependent on the knowledge of the degradation pathways that occur in solution, which can be retarded or eliminated by appropriate drying and excipients for stabilization. For vaccines, function is largely determined by immunogenicity and protection studies, rather than enzymatic activity. In the case of protein immunogens that are adsorbed to aluminum adjuvant crystals, the measurement of function and other parameters in vitro is correspondingly more difficult, since protein may be sequestered and difficult to remove for analysis. Thus, function can only be tested by immunogenicity and protection studies. The tertiary conformation of proteins can affect enzymatic functions, if present, but also can affect immunogenicity of B cell epitopes dependent on conformation. Linear B and T cell epitopes contained therein can be also affected by oxidation (of methionine and cysteine residues) and deamidation (especially of asparagine residues).

pH is one of the most critical formulation variables governing stability of therapeutic proteins. (Carpenter, Chang et al., 2002, Rational design of stable lyophilized protein formulations: theory and practice, *Pharm Biotechnol,* 13:109-33; Chi, Krishnan et al., 2003, Physical stability of proteins in aqueous solution: mechanism and driving forces in nonnative protein aggregation, *Pharm Res,* 20:1325-36) By affecting the conformational and colloidal stability of proteins in solution, pH can greatly modulate their aggregation rates (Chi, Krishnan et al., 2003, Physical stability of proteins in aqueous solution: mechanism and driving forces in nonnative protein aggregation, *Pharm Res,* 20:1325-36). In addition, rates of deamidation are strongly dependent on pH (Manning, Patel et al., 1989, Stability of protein pharmaceuticals, *Pharm Res,* 6:903-18). There can be different optimal pH values for physical and chemical stability for a given protein (Kolvenbach, Narhi et al., 1997, Granulocyte-colony stimulating factor maintains a thermally stable, compact, partially folded structure at pH2, *J Pept Res,* 50:310-8). For example, physical stability may be optimal at a pH where deamidation is unacceptably rapid (Chang, Reeder et al., 1996, Development of a stable freeze-dried formulation of recombinant human interleukin-1 receptor antagonist, *Pharm Res,* 13:243-9). In such cases, development of a lyophilized formulation where the rates of these reactions are minimized may provide a viable strategy to obtain a stable product. The few published studies examining effects of pre-lyophilization solution pH on the stability of therapeutic proteins during lyophilization and storage in dried formulations demonstrate the importance of this parameter (Prestrelski, Pikal et al., 1995, Optimization of lyophilization conditions for recombinant human interleukin-2 by dried-state conformational analysis using Fourier-transform infrared spectroscopy, *Pharm Res,* 12:1250-9; Chang, Reeder et al., 1996, Development of a stable freeze-dried formulation of recombinant human interleukin-1 receptor antagonist, *Pharm Res,* 13:243-9; Katayama, Kirchhoff et al., 2004, Retrospective statistical analysis of lyophilized protein formulations of progenipoietin using PLS: determination of the critical parameters for long-term storage stability, *J Pharm Sci,* 93:2609-23). These studies demonstrated the difficulty in identifying a pre-lyophilization solution pH that confers adequate physical and chemical stability to the proteins studied during lyophilization and storage. However, degradation of proteins could be minimized if sufficient amounts of stabilizing excipients are included in the formulation. For example, when recombinant human interleukin-1-receptor antagonist (rhIL-1ra) was formulated prior to lyophilization in a solution containing suboptimal sucrose at levels less than 0.3 mass ratio of sucrose/protein and at pH less than 6.5, severe protein aggregation occurred after lyophilization, during storage and reconstitution (Chang, Reeder et al., 1996, Development of a stable freeze-dried formulation of recombinant human interleukin-1 receptor antagonist, *Pharm Res,* 13:243-9). Protein aggregation was minimized following lyophilization from a solution at pH greater than 6, although, deamidation occurred at an unacceptably high rate. Following lyophilization from a solution containing amounts of sucrose greater than 0.3 sucrose/protein mass ratio at pH 6.5, both destabilization pathways could be inhibited. In another example, interleukin-2 (IL-2) had significantly greater structural perturbation during freeze-drying at pH 7, which resulted in higher levels of aggregation after storage and rehydration than samples lyophilized from solutions at pH 5 (Prestrelski, Pikal et al., 1995, Optimization of lyophilization conditions for recombinant human interleukin-2 by dried-state conformational analysis using Fourier-transform infrared spectroscopy, *Pharm Res,* 12:1250-9). The addition of sucrose to the pre-lyophilization solution formulation at pH 7 improved the stability of IL-2 during storage following lyophilization. More recently, this approach to preformulation has been taken with anthrax rPA to create a dried powder vaccine candidate for nasal administration (Jiang, Joshi et al., 2006, Anthrax vaccine powder formulations for nasal mucosal delivery, *J Pharm Sci,* 95:80-96). In this case, conditions for optimizing pH and excipient stabilizers were established for rPA in solution prior to lyophilization. As trehalose was one of the excipients determined to stabilize soluble rPA to thermal stress, there was evidence of at least 30 days stability at 40° C. for the dried trehalose-containing vaccines in terms of the total content of rPA in comparison to liquid samples in which rPA quickly disappeared. In an effort to obtain a dried powder composition for epidermal delivery using a gas-driven injection device, it was found that rapid freezing of aluminum-adsorbed hepatitis B vaccine (HBsAg) in the presence of a mixture of mannitol, glycine, and dextran (not more than ~6% w/v of total excipients) resulted in vaccines that retained particle size and relative immunogenicity in mice after a rapid freezing (spray freeze drying) that involved injection of the sprayed vaccine into liquid nitrogen prior to drying (Maa, Zhao et al., 2003, Stabilization of alum-adjuvanted vaccine dry powder formulations: mechanism and application, *J Pharm Sci,* 92:319-32). The behavior of the spray-freeze dried vaccines under thermal stress conditions was not determined, although normally lyophilized vaccine aggregated after processing and was minimally immunogenic. Diminished immunogenicity was associated with aluminum particle aggregation after reconstitution.

U.S. Pat. No. 6,890,512 ("Roser et al.") teaches lyophilization methods that will prevent aggregation of aluminum particles and further discloses a method of preventing gross aggregation during dehydration and rehydration of particulates in suspension by adding to a particulate suspension of aluminum hydroxide in excess of 15% (w/v) of trehalose. Trehalose, alpha.-D-glucopyranosyl-alpha-D-glucopyranoside, is a naturally occurring disaccharide responsible for protection of plant cells from desiccation. Trehalose has been shown to prevent denaturation of proteins during desiccation by forming sugar glasses that immobilize protein structure. However, Roser et al., while disclosing prevention of gross particle aggregation, did not disclose the importance of freezing rate of a particulate suspension or other factors critical to control and maintain pre-lyophilization particle size and protein structure in an aluminum-salts containing vaccine in the presence of trehalose. Maintenance of particle size is a critical parameter in controlling the degree of adsorption of protein immunogens to the surface of aluminum particles, and is influenced by several factors during lyophilization cycle in addition to the content of trehalose or other glassifying excipients. These factors influence the immunogenicity and generation of protective immune responses.

Multivalent vaccine compositions are known in the art and have been described in the literature. WO1993/024148 discloses an invention of multivalent vaccine containing antigens IPV-DPT-Hib-Hepatitis B wherein DPT is adsorbed to AIOH or aluminum phosphate and Hib is adsorbed to only aluminum phosphate, wherein the Hib antigen is used extemporaneously by mixing to the other antigens just prior to the administration.

WO1997/00697 discloses a DPT-Hib and pertussis multivalent vaccine adsorbed to aluminum phosphate, in which one container has a freeze-dried vaccine and the other container comprises a second antigen.

WO1998/000167 discloses a DTaP—IPV-Hib antigen vaccine and WO1999/13906 describes a multiple component vaccine in which certain components may be reconstituted from a lyophilized state by the other components of the vaccine, or may exist in a single solution, and administers the vaccine in a specially designed container at the time when the vaccination is performed.

WO2000/07623 describes a multi-component vaccine composition having acellular pertussis vaccine components (PT and FHA), diphtheria toxoid (DT), tetanus toxoid (TT), a conjugate of a capsular polysaccharide of *Haemophilus*

*influenzae* type b and tetanus toxoid or diphtheria toxoid (Hib), Hepatitis B Surface Ag (HBsAg) and inactivated poliovirus (IPV) which may be in a single solution, or certain components may be reconstituted from a lyophilized state by the other components of the vaccine.

WO2002/000249 discloses a capsular polysaccharide of *Haemophilus* influenza type b not adsorbed onto an aluminum adjuvant salt, and two or more further bacterial polysaccharides which may include whole cell pertussis, tetanus toxoid, diphtheria toxoid, Hepatitis B surface antigen (HbsAg), and/or conjugate polysaccharides of *N. meningitides* type A, or B, or C as antigens in a single quadrivalent and/or trivalent vaccine.

WO2006/097851 discloses a multivalent vaccine which can be prepared extemporaneously at the time of use by mixing together two components the first component comprising D, T, wP and HBsAg antigens and a second component comprising a Hib conjugate and one or more meningococcal conjugates.

WO2007/054820 relates to a vaccine composition wherein the D, T, and aP antigens are specifically adsorbed on aluminum hydroxide and the Hib and the Hep B antigens are adsorbed onto aluminum phosphate which do not exist in a fully liquid stable composition.

WO2008/044611 discloses a method for the preparation of a mixed IPV-DPT vaccine comprising an inactivated poliovirus Sabin strains type I, II, and III grown in Vero cells, a protective antigen against *Bordetella pertussis*, a diphtheria toxoid and a tetanus toxoid, which involves the step of producing a poliovirus Sabin strain having a high titer.

In the case of lyophilization, all the patent applications mentioned above require reconstitution of one or more of the individual components prior to administration of the vaccine. The mixing of antigenic components prior to administration from different vials results in the diminishment of the antibody titer against any particular antigen owing to interference of antigenic interactions. US Publication No. 2011/0206726A1 teaches a fully liquid hexavalent combination vaccine comprising D-T-aP-IPV, Hep B and Hib antigens wherein Hib is not substantially adsorbed to any adjuvant and D-T-aP adsorbed to AIOH and Hep B adsorbed to aluminum phosphate in a single vial. It also specifies that, antigenic competition in such multivalent vaccines often results in a diminished response to certain individual antigens. The patent application recognizes an inherent problem of mixing of lyophilized vaccines with liquid vaccines which represents supplementary constraint for the practitioner and involves a possibility of the same being carried out in a poor fashion. It also recognizes that the usage of multi-compartment syringes having separate chambers for liquid and lyophilized vaccines is too difficult to execute and no reduction in production costs (and by extension, no reduction of the cost of immunization) of the vaccine is possible.

The prior art is silent with respect to a combination vaccine comprising at least one antigen comprising a ribosome inactivating protein and at least one antigen comprising a toxin derived from bacterial spores.

Ricin is a plant toxin that is classified as a ribosome inactivating protein (RIP) and is a potent member of the AB family of toxins. Ricin is a highly toxic, naturally occurring lectin (a carbohydrate-binding protein) produced in the seeds of the castor plant *Ricinus communis*. Ricin is thought to be a bioterror threat because of its stability and high potency as well as the large worldwide reservoir created as a by-product of castor oil production. Exposure to ricin results in local tissue necrosis, and general organ failure leading to death within several days of exposure. A dose of purified ricin powder the size of a few grains of table salt can kill an adult human. The median lethal dose (LD50) of ricin if given by injection is around 22 micrograms per kilogram of body weight (1.78 mg for an average adult, around 1/228 of a standard aspirin tablet/0.4 g gross) in humans if exposure is from injection or inhalation. Ricin is toxic by all routes of exposure, but is especially toxic by the aerosol route, resulting in necrosis of lung epithelia within hours of exposure, multifocal hemorrhagic edema and death within 24-36 hours, with an estimated aerosol LD50 of 5-8 micrograms per kilogram of body weight (0.4 mg-0.64 mgs for an average adult).

The enzymatic A subunit (RTA) is an RNA-N-glycosidase which cleaves a specific adenine residue with eukaryotic 28S ribosomal RNA, leading to protein synthesis arrest and cell death. Depurination of this residue results in an immediate cessation of ribosome progression, which subsequently inhibits protein synthesis. Connected to RTA via a single disulfide bond, the B subunit (RTB) mediates binding to its cell surface receptor, terminal galactose and N-acetyl galactosamine moieties on glycoproteins and glycolipids. The ricin toxin B subunit (RTB) binds with micromolar affinity to $\alpha$(1-3)-linked galactose and N60 acetylgalactosamine residues that are expressed on the surface of all mammalian cell types. Binding of RTB to these receptors mediates internalization and retrograde transport of the ricin holotoxin to the endoplasmic reticulum (ER). In the ER, RTA dissociates from RTB and is retrotranslocated across the ER membrane into the cytosol where it gains access to rRNA targets. Ricin is therefore extremely potent, as it is able to internalize into almost all mammalian cell types. In addition to ribosome inactivating properties, ricin also elicits vascular leak syndrome (VLS), which primarily affects endothelial cells.

Antibodies to ricin, and more specifically the A chain of ricin, can prevent morbidity and mortality, if given passively prior to or very shortly after exposure, but the therapeutic window of opportunity post exposure is likely to be hours, prior to irreversible toxicity, lowering the probability of successful and effective post-exposure intervention. Data based on murine monoclonal antibodies to ricin A chain have indicated that antibodies that neutralize ricin toxin in vitro by inhibiting cytotoxicity of ricin on cultured cells can confer protection to mice by passive transfer. Equally important, non-neutralizing monoclonal antibodies do not confer protection. From these studies, it is inferred that a critical correlate of immunity that must be established in advanced animal models as well as human safety and immunogenicity studies is the capacity of a ricin vaccine to induce ricin neutralizing antibodies, in systemic circulation or located at mucosal surfaces. Further analysis have strongly suggests that the minority of the response to the ricin A chain results in neutralizing antibodies, and further that the neutralizing response is primarily against conformational determinants (O'Hara, Neal, et al., 2010, Folding domains within the ricin toxin A subunit as targets of protective antibodies, *Vaccine*, v 28:7035-46).

Analysis of mouse, rabbit and macaque sera has led to the identification of at least six immunodominant regions on RiVax™ comprising individual neutralizing and non neutralizing linear epitopes. Analysis available in the literature has also indicated human antibodies react with peptides spanning residues 41-90 (immunodominant region II) and 161-175 (immunodominant region IV), revealing some degree of common epitope recognition across species (Tommasi, Castelletti, et al., 2001, Identification of ricin A-chain HLA class II-restricted epitopes by human T-cell clones, *Clinical and Experimental Immunology*, v 125:391-400; Castelletti, Fracasso, et al., 2004, A dominant linear B-cell epitope of ricin A-chain is the target of a neutralizing antibody response in Hodgkin's lymphoma patients treated with an anti-CD25 immunotoxin, *Clinical and Experimental Immunology*, v 136:365-72). Immunodominant region II is located within folding domain I and contains a solvent-exposed α-helix (residues N97-F108) (O'Hara, Neal, et al., 2010, Folding domains within the ricin toxin A subunit as targets of protective antibodies, Vaccine), a target of the protective mAb R70 also known as Univax 70 (Lebeda and Olson, 1999, Prediction of a conserved, neutralizing epitope in ribosome-inactivating proteins, *Int J Biol Macromol,* v 24:19-26). Residues N97-F108 likely constitutes one of the most immunodominant regions on RTA. Immunodominant region IV on RTA spans amino acids I170-T190. There are at least two linear B-cell epitopes within this region. Residues L161 to I175, in particular, were identified as being a conserved target of serum Abs from Hodgkin's lymphoma patients who had been treated with deglycosylated RTA (RTA.dg) immunotoxin (Castelletti, Fracasso, et al., 2004, A dominant linear B-cell epitope of ricin A-chain is the target of a neutralizing antibody response in Hodgkin's lymphoma patients treated with an anti-CD25 immunotoxin, *Clin. Exp. Immunol, v* 136:365-72). A murine $IgG_1$ mAb GD12 was effective in protecting mice against the effects of intraperitoneal and intragastric ricin challenges, thereby establishing that preexisting serum Abs directed against residues in immunodominant region IV are sufficient to confer both systemic and mucosal immunity to ricin, at least in rodents (Neal, O'Hara, et al., 2010, A monoclonal immunoglobulin G antibody directed against an immunodominant linear epitope on the ricin A chain confers systemic and mucosal immunity to ricin, *Infect Immun*, v 78:552-61). The GD12 epitope is situated within α-helix E, which runs through the core of RTA's domain II and which terminates with two residues (Glu177 and Arg180) that are involved in RTA catalytic activity (O'Hara, Neal, McCarthy, Kasten-Jolly, Brey and Mantis, 2010, Folding domains within the ricin toxin A subunit as targets of protective antibodies, *Vaccine*; Katzin, Collins, et al., 1991, Structure of ricin A-chain at 2.5 A, Proteins., v 10:251-9; Li, Chiou, et al., 2009, A two-step binding model proposed for the electrostatic interactions of ricin a chain with ribosomes, *Biochemistry*, v 48:3853-63).

There is a general consensus that protection against gastrointestinal or aerosol exposure to ricin requires antibodies in respiratory or gastrointestinal secretions that effectively intercept ricin before it can adversely affect epithelial tissue (Griffiths, Bailey, et al., 1997, Liposomally-encapsulated ricin toxoid vaccine delivered intratracheally elicits a good immune response and protects against a lethal pulmonary dose of ricin toxin, Vaccine, v 15:1933-9; Griffiths, Bailey, et al., 1998, Local and systemic responses against ricin toxin promoted by toxoid or peptide vaccines alone or in liposomal formulations, *Vaccine*, v 16:530-5; Griffiths, Phillips, et al., 1999, Comparison of the quality of protection elicited by toxoid and peptide liposomal vaccine formulations against ricin as assessed by markers of inflammation, *Vaccine*, v 17:2562-8; Poli, Rivera, et al., 1996, Aerosolized specific antibody protects mice from lung injury associated with aerosolized ricin exposure, *Toxicon*, v 34:1037-44; Yan, Rill, et al., 1996, Intranasal stimulation of long-lasting immunity against aerosol ricin challenge with ricin toxoid vaccine encapsulated in polymeric microspheres, *Vaccine*, v 14:1031-8.). In rodents (Griffiths, Phillips and Bailey, 1999, Comparison of the quality of protection elicited by toxoid and peptide liposomal vaccine formulations against ricin as assessed by markers of inflammation, Vaccine, v 17:2562-8; Brown and White, 1997, Ultrastructure of rat lung following inhalation of ricin aerosol, *International Journal of Experimental Pathology*, v 78:267-76; DaSilva, Cote, et al., 2003, Pulmonary gene expression profiling of inhaled ricin, Toxicon, v 41:813-22; Doebler, Wiltshire, et al., 1995, The distribution of [125I]ricin in mice following aerosol inhalation exposure, *Toxicology*, v 98:137-49) (Wilhelmsen and Pitt, 1996, Lesions of acute inhaled lethal ricin intoxication in rhesus monkeys, *Veterinary Pathology*, v 33:296-302), ricin inhalation results in respiratory distress and airway and pulmonary lesions. Inhalation of ricin in rats leads to rapid apoptotic changes in alveolar macrophages within 6 hours after exposure, finally culminating in inter alveolar edema at 12 and 15 h after exposure, mixed inflammatory cell infiltrates, alveolar flooding followed by tissue necrosis (Brown and White, 1997, Ultrastructure of rat lung following inhalation of ricin aerosol, *International Journal of Experimental Pathology*, v 78:267-76.). Compared to aerosol exposure, ricin administered orally is considerably less toxic (Balint, 1974, Ricin: the toxic protein of castor oil seeds, *Toxicology*, v 2:77-102). The literature indicates that the oral $LD_{50}$ is 20 mg/kg, ~1000 fold higher than the aerosol or systemic LDso values. Ingestion of whole castor beans results in severe abdominal pain, vomiting, diarrhea, and (depending on the number of beans and degree of mastication) death (Audi, Belson, et al., 2005, Ricin poisoning: a comprehensive review, *JAMA, v* 294:2342-51; Bradberry, Dickers, et al., 2003, Ricin poisoning, *Toxicological Reviews*, v 22:65-70; Mantis, 2005, Vaccines against the category B toxins: Staphylococcal enterotoxin B, epsilon toxin and ricin, *Advanced Drug Delivery Reviews*, v 57:1424-39; Olsnes, 2004, The history of ricin, abrin and related toxins, Toxicon, v 44:361-70). Rats challenged with ricin by gavage (1-30 mg/kg) developed dose-dependent lesions in the stomach and proximal small intestine (Sekine, Kawase, et al., 1986, Pathological study on mucosal changes in small intestine of rat by oral administration of ricin. I. Microscopical observation, *Acta Pathol Jpn*, v 36:1205-12), leading to widespread intestinal villus atrophy, crypt elongation, sloughing of the epithelium, and infiltration of inflammatory cells, including eosinophils and neutrophils (Sekine, Kawase, Nishimori, Mitarai, Harada, Ishiguro and Kikutani, 1986, Pathological study on mucosal changes in small intestine of rat by oral administration of ricin. I. Microscopical observation, *Acta Pathol Jpn*, v 36:1205-12; Ishiguro, Harada, et al., 1984, Effects of ricin, a protein toxin, on glucose absorption by rat small intestine. (Biochemical studies on oral toxicity of ricin. II), *Chem Pharm Bull* (*Tokyo*), v 32:3141-7; Ishiguro, Mitarai, et al., 1983, Biochemical studies on oral toxicity of ricin. I. Ricin administered orally can impair sugar absorption by rat small intestine, *Chem Pharm Bull* (*Tokyo*), v 31:3222-7; Ishiguro, Nakashima, et al., 1992, Interaction of toxic lectin ricin with epithelial cells of rat small intestine in vitro, *Chem Pharm Bull* (*Tokyo*), v 40:441-5; Ishiguro, Tanabe, et al., 1992, Biochemical studies on oral toxicity of ricin. IV. A fate of orally administered ricin in rats, *Journal of Pharmacobio-Dynamics*, v 15:147-56). Similar histopathologic changes have been observed in mice challenged intragastrically with ricin (Yoder, Aslam, et al., 2007, Evidence for widespread epithelial damage and coincident production of monocyte chemotactic protein 1 in a murine model of intestinal ricin intoxication, *Infection and Immunity*, v 75:1745-50). It is postulated that following intestinal exposure, ricin ultimately disseminates from the mucosa into circulation (Ishiguro, Tanabe, Matori and Sakakibara, 1992, Biochemical studies on oral toxicity of ricin. IV. A fate of orally administered ricin in rats, *Journal of Pharmacobio-Dynamics*, v 15:147-56), since ricin has been shown to cross polarized epithelial cell monolayers in vitro (Mantis, McGuinness, et al., 2006, Immunoglobulin A antibodies against ricin A and B subunits protect epithelial cells from ricin intoxication, *Infection and Immunity*, v 74:3455-62; van Deurs, Hansen, et al., 1990, Endocytosis, intracellular transport and transcytosis of the toxic protein ricin by a polarized epithelium, *Eur J Cell Biol*, v 51:96-109). The inherent resistance of the gastrointestinal tract to ricin is likely due to a number of factors that impede toxin absorption, including intestinal proteases, digestive enzymes, mucus, and secretory IgA, whose galactose-rich oligosaccharide can competitively inhibit ricin attachment to the apical surfaces of intestinal epithelial cells (Mantis, Farrant, et al., 2004, Oligosaccharide side chains on human secretory IgA serve as receptors for ricin, *Journal of Immunology*, v 172:6838-45).

Efforts to create a vaccine against ricin have mostly focused on the RTA subunit. Two mutant versions of RTA have been extensively studied for their ability to promote antibody mediated immunity to ricin. One mutant, RVEc, completely removes the third folding domain, which mediates binding to RTB but is only targeted by non-neutralizing antibodies. A highly immunogenic loop in the first domain, which is also targeted only by non-neutralizing antibodies, is also removed. Another mutant, used in RiVax™, retains the entire structure of native RTA but contains two point mutations, Y80A and V76M, which completely remove both of RTA's known toxicities, ribotoxicity and vascular leak induction respectively. Studies in mice and rabbits demonstrated that RiVax™ is safe and immunogenic when administered by the intramuscular (i.m.) and intradermal (i.d.) routes. In a Phase I clinical trial, not all participants responded to RiVax™ when employed as an i.m. vaccine. In a second Phase I trial in which individuals received three i.m. immunizations over a span of 26 weeks, it was demonstrated that adsorption of RiVax™ to aluminum salt adjuvants enhanced RiVax™-specific serum antibodies (Ab) titers. The levels of anti-RiVax™ Ab were neither robust nor long lasting. Moreover, levels of toxin-neutralizing Ab were also extremely low in RiVax™-immunized individuals. Ricin neutralizing antibodies are likely the primary determinant of protective immunity to ricin. Collectively, these data defined the need to identify new adjuvants to boost the efficacy of RiVax™ and other antigens derived from ribosome inactivating proteins.

Anthrax is an acute infectious disease that is easily transmitted to humans by environmentally durable spores produced by gram positive bacterium *Bacillus anthracis*. Because the spores are robust and contagious, anthrax is considered a Category A bioterror threat. Anthrax infection can occur in three forms: cutaneous (skin), inhalation, and gastrointestinal. Inhaled spores can cause a rapidly progressing form of anthrax since the spores are transported to lymph nodes near the lungs where they germinate, releasing vegetative bacteria into the bloodstream. After infection in the bloodstream, the bacteria synthesize a complex series of toxin components that make up anthrax toxin, resulting in overwhelming toxemia that causes shock and organ failure.

The bacterium secretes 3 proteins which can combine to form two binary toxins, which cause the major pathology during anthrax infection of humans and animals. The cell binding component is Protective Antigen (PA), and once bound it is cleaved by a cell surface furin-like protease, leaving behind a 63 kDa fragment which then heptamerizes. The surface of the heptamer can bind up to 3 copies of edema factor (EF) and/or lethal factor (LF), forming edema toxin or lethal toxin, respectively. EF is an adenylate cyclase which increases intracellular cAMP concentrations. LF is a zinc-dependent metalloprotease which cleaves members of the MAPKK pathway, leading to apoptosis. Antibodies targeting PA can neutralize both toxins, and thus recombinant PA is the major antigen in the currently licensed anthrax vaccine adsorbed (AVA, Biothrax®). However, a six-dose vaccination series is required to sustain a high anti-PA IgG titers.

Treatment of anthrax involves long-term antibiotic therapy, since ungerminated spores can lie dormant in the lungs for up to 60 days. Only a few inhaled spores can cause inhalational anthrax poisoning. Once the toxin has entered the bloodstream, antibiotics are ineffective, and only toxin-specific therapy is effective. Passively transferred antibodies can neutralize anthrax toxins and can be used post-exposure in conjunction with antibiotics. Because of the long residence time of spores in the lung, it is possible to vaccinate post-exposure, but the onset of neutralizing antibodies must occur during the period of antibiotic therapy. Thus, there is a need for effective anthrax vaccines that can elicit rapid protective immunity. Moreover, there is a need for vaccine formulations that can be stored for extended periods prior to distribution, including vaccines intended to be used in "post-event" or "post-exposure" instances where vaccines would be deployed from the Strategic National Stockpile after weaponized use of hazardous biologicals. These products are currently stockpiled under environmentally controlled (cold chain) refrigerated storage conditions until those unpredictable events would occur, imposing huge logistical demands on maintaining the stockpile for those targeted interventions. Vaccines to be stored in the Strategic National Stockpile and used under emergency situations for biodefense are preferred to have long-term shelf life.

It is well accepted that PA is the dominant immunogen in AVA and target for protective immunity in pre-exposure and post exposure prophylaxis as a single component recombinant vaccine. Several aluminum adsorbed recombinant PA vaccines, based on expression of native PA in avirulent *B. anthracis* or *E. coli*, have been manufactured and tested in recent Phase I trials. Aluminum-adjuvant PA vaccines have been shown to be immunogenic in relationship to AVA, but it is difficult to directly state with the current evidence that an aluminum-adsorbed PA vaccine will in fact be the successor to AVA (Brown, Cox, et al., Phase I study of safety and immunogenicity of an *Escherichia coli*-derived recombinant protective antigen (rPA) vaccine to prevent anthrax in adults, *PLoS One*, v 5:e13849; Campbell, Clement, et al., 2007, Safety, reactogenicity and immunogenicity of a recombinant protective antigen anthrax vaccine given to healthy adults, *Hum Vaccin*, v 3:205-11; Gorse, Keitel, et al., 2006, Immunogenicity and tolerance of ascending doses of a recombinant protective antigen (rPA102) anthrax vaccine: a randomized, double-blinded, controlled, multicenter trial, *Vaccine*, v 24:5950-9). Limitations noted in the development of recombinant PA based vaccines have been rapid deamidation of rPA and loss of potency of liquid aluminum adsorbed vaccine. Therefore, the overall potency and related immunological correlates of effectiveness for any PA vaccine are still undeveloped. Improvements in the AVA vaccine have been directed at modifying the schedule of vaccination such that the current recommendation (by the FDA and the CDC) for AVA eliminated the requirement for a second vaccination at day 14 and changed the administration from subcutaneous to intramuscular. This first generation product is now approved for a vaccination regimen that involves injection by the intramuscular route at 0, 4 weeks, 6 months, and booster doses at 12 and 18 months (Marano, Plikaytis, et al., 2008, Effects of a reduced dose schedule and intramuscular administration of anthrax vaccine adsorbed on immunogenicity and safety at 7 months: a randomized trial, *JAMA*, v 300:1532-43). The changes were implemented following extensive study of AVA showing non inferiority of the 0, 4 i.m. regimen. The vaccine is routinely used in the USA for military personnel and has been acquired by HHS for the stockpile for civilian use in the event of a terrorist event and could be given upon Emergency Use Authorization (EUA) for post exposure prophylaxis (PEP) in conjunction with antibiotic therapy, prior to the time that FDA licensure is achieved for that indication. The ACIP has recommended the 0, 2, 4 week AVA subcutaneously for PEP along with a 60 day course of antibiotics. Using the currently licensed vaccination regimen with AVA, peak antibody titers are reached by week six through eight (after two injections), similar to peak titers reached using the former 0, 2, 4 week subcutaneous vaccination regimen (Marano, Plikaytis, Martin, Rose, Semenova, Martin, Freeman, Li, Mulligan, Parker, Babcock, Keitel, El Sahly, Poland, Jacobson, Keyserling, Soroka, Fox, Stamper, McNeil, Perkins, Messonnier and Quinn, 2008, Effects of a reduced dose schedule and intramuscular administration of anthrax vaccine adsorbed on immunogenicity and safety at 7 months: a randomized trial, *JAMA*, v 300:1532-43). Although antibodies decline until booster doses are given at 6, 12, and 18 months, it is presumed that protection against anthrax spore exposure has been achieved by the full regimen. Although no precise correlate of antibody-mediated immunity has been defined in non-human primate or rabbit models, protective titers in human subjects may be reached after two or three doses of AVA/Biothrax®.

A notable improvement in the AVA vaccine has been reported by adding immunostimulatory CpG sequences to AVA (Rynkiewicz, Rathkopf, et al., 2011, Marked enhancement of the immune response to BioThrax® (Anthrax Vaccine Adsorbed) by the TLR9 agonist CPG 7909 in healthy volunteers, Vaccine, v 29:6313-20; Klinman, Xie, et al., 2006, CpG oligonucleotides improve the protective immune response induced by the licensed anthrax vaccine, *Ann N Y Acad Sci*, v 1082:137-50; Klinman, Xie, et al., 2004, CpG oligonucleotides improve the protective immune response induced by the anthrax vaccination of Rhesus macaques, *Vaccine*, v 22:2881-6). Vaccination with modified product (AV7909) resulted in a demonstrably accelerated immune response in relationship to AVA achieving titers of TNA equivalent to peak AVA titers in approximately 21 days (after two doses of AVA7909 vaccine) (Rynkiewicz, Rathkopf, Sim, Waytes, Hopkins, Giri, DeMuria, Ransom, Quinn, Nabors and Nielsen, 2011, Marked enhancement of the immune response to BioThrax® (Anthrax Vaccine Adsorbed) by the TLR9 agonist CPG 7909 in healthy volunteers, Vaccine, v 29:6313-20). Further, peak titers of TNA were 6-8 fold higher using the AVA7909 vaccine, whereas at the same time AV7909 was associated with a higher frequency of injection site reactions. The modification of PA-based subunit vaccines with safe and effective adjuvants is thus encouraged by the results so far obtained with AV7909.

U.S. Pat. No. 7,037,503 ("Collier et al") discloses dominant negative inhibitor (DNI) mutations of recombinant PA in which mutations of PA result in inhibition of its pore-forming ability, in which the mutations result in a PA molecule that is therapeutic for the treatment of toxemia caused by the secretion of anthrax toxins by bacteria circulating in the bloodstream of animals and humans afflicted with anthrax disease.

In an effort to improve upon anthrax vaccine, a dominant negative inhibitor (DNI) of PA has been developed. The anthrax DNI is an analog of rPA containing two mutations that prevent pore formation and translocation of the holotoxin in the cytosol. DNI binds to the same cell-surface receptors with the same affinity as PA and can form self-assembled heptamers on the surface of cells. The absence of the translocation step prevents DNI-dependent transport of Edema Factor and/or Lethal Factor into cell cytoplasm. Hence, complexes of DNI with LF or EF are nontoxic. DNI was originally proposed for use as an intravenous agent for post-aerosol exposure to anthrax spores to block holotoxin, since one subunit of DNI could block PA-dependent pore formation after heptamerization. It has been shown that animals vaccinated with the DNI antigen induced higher levels of antibodies to toxin and maintained high levels of protective antibody titers for up to one year without booster injections of antigen. The hyperimmunogencity of DNI has been attributed to the defects in pore formation which may enable more efficient antigen presentation in the context of class II MHC.

The anthrax DNI variant of recombinant PA was originally isolated by Collier et al. at Harvard in a screen for mutants of PA that were defective the steps of binding, transporting or internalization from the endosome (Sellman, Mourez, et al., 2001, Dominant-negative mutants of a toxin subunit: an approach to therapy of anthrax, Science, v 292:695-7; Mourez, Kane, et al., 2001, Designing a polyvalent inhibitor of anthrax toxin, *Nat Biotechnol*, v 19:958-61). Mutated residues 397 and 425 in DNI are located in domain II, the pore-forming domain (Mourez, Yan, et al., 2003, Mapping dominant-negative mutations of anthrax protective antigen by scanning mutagenesis, *Proc Natl Acad Sci USA*, v 100:13803-8). Subsequent study revealed the substitution of DNI for one or more of the wild-type PAs within the heptamer blocked the movement of the toxin across endosomal membranes, effectively blocking the toxicity caused by liberation of LF and EF into the cell cytosol. It is hypothesized that these two mutations inhibit the essential conformational change of $(PA63)_7$ from a ring-shaped core to a β barrel structure and thus prevent the heptamer from inserting itself into the endosomal membrane (Sellman, Nassi, et al., 2001, Point mutations in anthrax protective antigen that block translocation, *J Biol Chem, v* 276:8371-6). Consequently, these mutations inhibit the translocation of LF or EF to the cytosol and prevent cytotoxicity (Sellman, Mourez and Collier, 2001, Dominant-negative mutants of a toxin subunit: an approach to therapy of anthrax, *Science*, v 292:695-7; Mourez, Kane, Mogridge, Metallo, Deschatelets, Sellman, Whitesides and Collier, 2001, Designing a polyvalent inhibitor of anthrax toxin, *Nat Biotechnol*, v 19:958-61; Sellman, Nassi and Collier, 2001, Point mutations in anthrax protective antigen that block translocation, *J Biol Chem*, v 276:8371-6). The DNI protein is activated normally, undergoes heptamerization, and binds LF and EF. The assembled complexes are endocytosed and trafficked to an acidic compartment similar to wild type PA. Upon exposure to acidic conditions, however, the complexes do not undergo membrane insertion or pore formation, and are not able to translocate the LF and EF into the cytosol. Thus, toxicity is completely blocked. The inactive, dead-end anthrax toxin complexes are believed to be trafficked to lysosomes and metabolized. DNI works in a dominant fashion meaning that DNI can be present in significantly lower concentrations than wt PA and still be effective in blocking toxin action. Studies performed in Fisher 344 rats subjected to challenge with LT (PA and LF) and administered DNI initially suggested a potential use of DNI in the treatment of patients infected with *B. anthracis* (Sellman, Mourez and Collier, 2001, Dominant-negative mutants of a toxin subunit: an approach to therapy of anthrax, *Science*, v 292:695-7). The DNI protein was developed on the basis that it could be used as a post exposure prophylaxis, and confirmatory studies were reported rats and then in rabbits with spore challenge. Subsequent to the rabbit and rat studies, several preliminary studies were conducted in mice and showed that the DNI mutant, with aluminum was more immunogenic than wild type PA (Aulinger, Roehrl, et al., 2005, Combining anthrax vaccine and therapy: a dominant-negative inhibitor of anthrax toxin is also a potent and safe immunogen for vaccines, *Infect Immun*, v 73:3408-14; Yan, Roehrl, et al., 2008, Selection and evaluation of the immunogenicity of protective antigen mutants as anthrax vaccine candidates, *Vaccine*, v 26:947-55). The DNI variant of PA induced 4-5 more anti-PA antibodies than the aluminum adsorbed PA vaccines. Increased immunogenicity could be due to that fact that the DNI PA does not escape the endosome and is more efficiently processed and presented to MHC molecules in antigen presenting cells.

In preclinical studies of PA or rPA vaccine, a spectrum of adjuvant formulations has been evaluated in relationship to aluminum-based adjuvants. A significant increase in toxin neutralizing antibody (TNA) titers in mice was obtained when CpG oligodeoxynucleotide adjuvant was added directly to AVA (Klinman, Klaschik, et al., 2010, Immunostimulatory CpG oligonucleotides: Effect on gene expression and utility as vaccine adjuvants, *Vaccine*, v 28:1919-23). These studies also demonstrated longer lasting TNA and increased protection from anthrax challenge when antibody levels had waned below the usually associated protective levels in mice, suggesting the induction of long-lasting memory B cells. Continuing Phase I studies have also demonstrated that CpG sequences with AVA induce higher TNA and ELISA antibodies resulting in a more rapid time to peak antibody levels. In addition to studies with aluminum adjuvants and CpG, studies conducted in the late 90s in Rhesus macaques indicated the saponin adjuvant, QS-21, and the partially detoxified lipid A (monophosphoryl lipid A/MPL) (Ivins, Pitt, et al., 1998, Comparative efficacy of experimental anthrax vaccine candidates against inhalation anthrax in Rhesus macaques, *Vaccine*, v 16:1141-8) could induce protection in comparison to unformulated rPA. Taken together, these data point to the need for additional adjuvants, and a need to control the factors that affect vaccine efficacy.

With respect to vaccines for anthrax and ricin, both of these vaccines are being developed individually and would be useful for military personnel and emergency first responders and in the event of dissemination of either biothreat agent during a biological attack. Thus it would be extremely useful if the vaccines could be administered simultaneously without compromising the response to either vaccine while still providing protection against whichever toxin might be encountered. There remains a need for a unique combination vaccine that is safe and effective against ricin and anthrax exposure and is capable of inducing neutralizing antibodies required for robust protection and vaccine efficacy. The combination will permit the concurrent immunization with fewer injections that would otherwise be needed with individual vaccine components.

SUMMARY OF THE INVENTION

The present invention provides for a stable immunogenic composition capable of eliciting a robust and durable immune response yielding a measurable increase in neutralizing antibodies at least 200 days post-administration, comprising at least one antigen consisting of a ribosome inactivating protein and at least one antigen comprising a toxin derived from bacterial spores. Optionally, the immunogenic composition comprises a first antigen comprising a ribosome inactivating protein and a second antigen comprising a toxin derived from bacterial spores. In an alternative embodiment, the composition yields a measurable increase in neutralizing antibodies to the first antigen comprising the ribosome inactivating protein. In another embodiment, the composition is capable of yielding a measurable increase in neutralizing antibodies to the second antigen comprising a toxin derived from bacterial spores. In yet another embodiment, the composition is capable of yielding a measurable increase in neutralizing antibodies to both the first and the second antigen. Optionally, the composition of the present invention elicits a measurable increase in neutralizing antibodies to the first antigen at least 200 days post-administration. Alternatively, the composition of the present invention elicits a measurable increase in neutralizing antibodies to the second antigen at least 200 days post-administration. In yet another embodiment, the composition of the present invention elicits a measurable increase in neutralizing antibodies to the first and the second antigen at least 200 days post-administration.

One additional aspect of the present invention provides for a method of eliciting a stable immune response yielding a measurable increase in neutralizing antibodies at least 200 days post-administration, comprising providing an immunogenic composition comprising at least one antigen comprising a ribosome inactivating protein and at least one antigen comprising a toxin derived from bacterial spores and administering the immunogenic composition to an individual.

In yet another aspect, the present invention provides for a process for formulating a vaccine composition comprising: providing a ricin A chain derived from ricin toxin; providing an effective amount of dominant negative inhibitor (DNI) protein derived from *Bacillus anthracis*; formulating (a) and (b) as a dried product for reconstitution using an excipient selected from the group consisting of mannitol and sucrose and a buffer; and providing at least one adjuvant to (a) and (b).

DETAILED DESCRIPTION OF THE INVENTION

Figure 1:
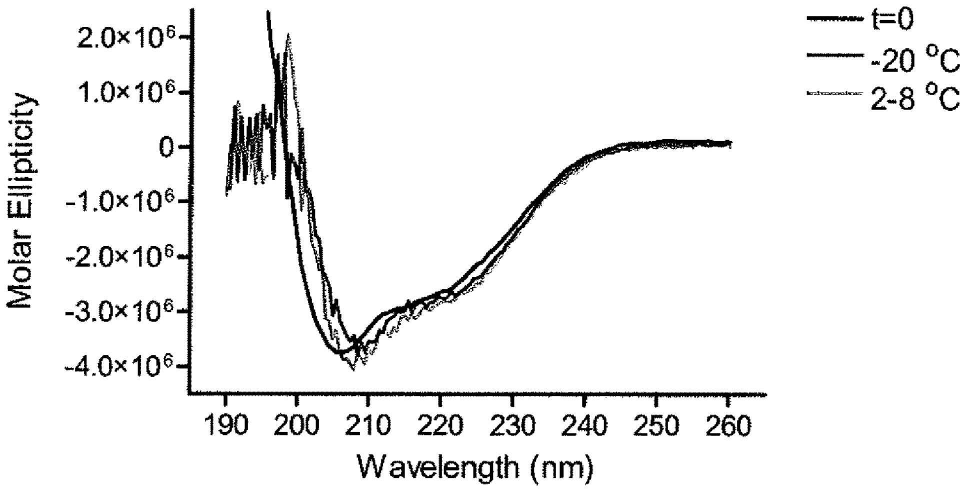
FIG. 1 consists of CD spectroscopy data of stability samples at 24 months.

The present invention is directed towards a combination vaccine that comprises vaccine components that are suitable for the prevention, amelioration and treatment of exposure to toxins consisting of ribosome inactivating proteins and concurrently exposure to toxins elaborated by spore forming bacteria. The vaccine of the present invention elicits protective immunity to each of the antigenic components without causing immune interference after administration to an individual. In a preferred embodiment, the combination vaccine is administered prior to exposure to the toxin or infectious agent. In another aspect of the invention, the vaccine can be administered after exposure to the toxin or infectious agent. Further, in another embodiment of the invention, the vaccine can be administered after exposure to the infectious agent or toxin in combination with therapies intended to cure or ameliorate the effects of the toxins that are responsible for the morbidity of disease exposure.

In another embodiment of the current invention, the combination vaccine is formulated with adjuvants that preferentially induce neutralizing antibodies against the corresponding antigenic vaccine ingredients.

In a preferred embodiment of the current invention, the combination vaccine is formulated with antigen derived from ricin toxin, consisting of the purified ricin A chain combined with antigen consisting of the protective antigen (PA) derived from *Bacillus anthracis.*

The advantages of the present invention include a combination vaccine which can confer protection against exposure to toxins of that are secreted by *Bacillus anthracis* during infection and exposure to ribosome inactivating proteins.

The vaccine of the invention provides protective immune responses to toxins with no interference or immune competition among the antigens that are present in the vaccine. Thus, a single shot will confer immunogenicity simultaneously in a single administration against anthrax diseases and exposure to ricin toxin. The vaccine is easier to administer in fewer injections to achieve protective and long lasting immunity to ribosomal inactivating toxins and the toxins causing pathology against anthrax disease upon exposure to spores of *Bacillus anthracis*. Since a single shot would afford immunity against anthrax and ribosome inactivating proteins, the cost of vaccination would be reduced. The vaccine of the present invention would be advantageous by reducing the number of visits required for full vaccination and the numbers of vaccine administrations necessary to achieve full protection. Thus, the present invention provides a vaccine that is more acceptable for rapid onset of protective immunity.

The following examples illustrate the various embodiments of the present invention and are not meant to be limiting in scope based on such examples.

Example I: Production of Vaccine Antigen Ricin a Chain

Ricin A chain is structurally unstable, with improvements being necessary to achieve the objective of long lasting and rapid onset immunity using 2 vaccine doses or fewer. The ricin A chain is extremely labile in aqueous buffers without stabilizers, leading to unfolding and aggregation of the protein in solution. Protein unfolding also occurs on the surface of aluminum adjuvant particles in the liquid suspension vaccines. The summation of the studies with liquid aluminum-adsorbed vaccine in mice, rabbits, humans and macaques indicate that improvements will be necessary to achieve the objective of long lasting and rapid onset immunity using two vaccine doses or fewer. Because the effectiveness of ricin A chain vaccine is thought to be associated with protein configuration, as the majority of neutralizing antibodies recognize conformational determinants, efforts were initiated to stabilize RiVax™ bound to conventional aluminum adjuvant by lyophilization. During lyophilization, aggregation of colloidal aluminum hydroxide suspensions can be inhibited by reducing the extent of their freeze-concentration by using formulations that contain high concentrations of glass-forming excipients, and by limiting the time over which the freeze-concentrated suspensions can aggregate by using rapid cooling procedures to maximize the kinetics of glass formation (Clausi, Cummiskey, et al., 2008, Influence of particle size and antigen binding on effectiveness of aluminum salt adjuvants in a model lysozyme vaccine, *J Pharm Sci*, v 97:5252-62; Clausi, Merkley, et al., 2008, Inhibition of aggregation of aluminum hydroxide adjuvant during freezing and drying, *J Pharm Sci*, v 97:2049-61). This has been usually accomplished by freeze drying in the presence of disaccharides such as trehalose and other excipients that promote a glass state during process and storage. Proteins can be stored for long-term as long as the product is stored below its glass transition temperature ($T_g$), above which the material transitions into a rubbery state.

A small scale process for purifying RiVax™ was developed and implemented for initial human Phase 1 trials (Smallshaw, Richardson, et al., 2005, Preclinical toxicity and efficacy testing of RiVax™, a recombinant protein vaccine against ricin, Vaccine, v 23:4775-84; Vitetta, Smallshaw, et al., 2006, A pilot clinical trial of a recombinant ricin vaccine in normal humans, *Proceedings of the National Academy of Sciences of the United States of America*, v 103:2268-73). During these initial small Phase 1 studies in humans, the vaccine purification process was improved and scaled up to increase protein yields and to develop an aluminum-adsorbed product. In the process of developing the RiVax™ vaccine candidate, the bulk drug substance was stabilized in aqueous buffer by the inclusion of 50% glycerol (Peek, Brey, et al., 2007, A rapid, three-step process for the preformulation of a recombinant ricin toxin A-chain vaccine, *Journal of Pharmaceutical Sciences*, v 96:44-60) which was removed by the final process to make vaccine adsorbed to Alhydrogel®. Because of the potential impact of destabilization in liquid buffers and the potential importance of conformational determinants, a major effort has been undertaken to stabilize RiVax™ adsorbed to Alhydrogel®.

A robust and scalable process was developed for the purification of RiVax™, a ricin A chain mutant vaccine candidate. The purified RiVax™ is stored in 50% glycerol for further formulation development and processing in the generation of RiVax™, AIOH adsorbed or RiVax™-TR, (aluminum-adsorbed, lyophilized for reconstitution). RiVax™ is stored in glycerol at −20° C., and is subject to dialysis or ultrafiltration to remove glycerol before adsorption to AIOH and further processing and vial filling. The rationale for the use of glycerol concerns identifying conditions for the retention of RiVax™ structure during storage prior to aluminum adsorption under conditions in which the protein does not significantly aggregate or unfold. These conditions were identified in extensive screens of conditions to examine tertiary conformation, secondary protein structure aggregation and the influence of generally regarded as safe (GRAS) excipients on possible unfolding events. Through screens, it was found that the most efficient stabilizer was glycerol for the retention of native structure. It may be possible to further scale up runs to eliminate the glycerol holding/storage step in favor of direct absorption to AlOH, which may stabilize protein structure and immunogenicity.

A recombinant *E. coli* process was developed for the manufacture of RiVax™ according to principles of rational design. This process is suitable for implementation within a GMP manufacturing environment and has been implemented in 7, 100 liter (L) runs, 4 of which were conducted as process development runs to scale up from 10 L, and 2 were conducted in a cGMP environment as engineering or demonstration runs, and one run was conducted under cGMP. All runs were conducted at the Cambrex/Lonza facility in Baltimore, Md. Material generated from one of the process development runs has been established as a reference protein, and material generated from one of the engineering runs has been used extensively in adjuvant formulation characterization Strain construction and fermentation development proceeded according to the following protocol: Initially, the coding sequence for the mature RiVax™ protein with mutations Y80A/V76M was cloned into the pET28a vector and transformed and stored in the *E. coli* strain BL21(DE3) at the University of Texas Southwestern Medical Center (UTSWMC). The product was expressed in recombinant *E. coli* BL21(DE3) with low yields, approximately 6 mg/L. The host strain BL21(DE3) can shed phage particles under certain stress conditions and is thus not suitable for cGMP manufacturing at large scale in multi-use facilities. The pET28a-Y80A/V76M construct was transformed into BLR (DE3) and HMS174(DE3), which are recA- and do not shed phage particles, and evaluated for product expression. Eight colonies from each transformation were streaked onto LB Kan agar and four well-isolated colonies from each transformation were grown out in 0.5× Vegan TB with 50 mg/L kanamycin for IPTG-inducible RiVax™ expression analysis by SDS-PAGE. Post-induction samples were taken 3.0 to 3.5 hours after the addition of IPTG and samples were analyzed by SDS-PAGE for product expression. A protein of approximately 30 kDa was clearly induced in each of these cultures. The insert sequence from both the BLR 3 and HMS174 A clones was 100% homologous with the predicted sequence.

Fermentation development and optimization was conducted with the goals of increasing the cell mass and the fermentation titer of RiVax™, as well as developing scalable methods for RiVax™ recovery in a soluble form using cGMP compliant medium and process. Fermentations were performed in B. Braun fermenters at the 10 L scale in batch and fed-batch mode with varying inducer (IPTG) concentration. The main variables that were examined included 1) sources of peptone from non-animal origin 2) concentration of IPTG inducer and 3) carbon source. Batch fermentations were performed for one clone from each of the *E. coli* host strains: Clone BLR 3 and Clone HMS A. Starter cultures of ECPM medium (25 mL) were inoculated with 0.25 mL of either BLR 3 or HMS A frozen stock culture and grown 10 hours at 37° C., 200 RPM in a gyratory shaker. These cultures were used to inoculate 200 mL of Batch Fermentor Medium in 1000 mL baffled shake flasks. The 200 mL cultures were allowed to grow at 37° C., 200 RPM for nine hours then used to inoculate 10 L of Batch Fermentation Medium in 14 L BIOFLO 3000 vessels (New Brunswick Scientific). Casamino Acids and other non-animal origin nitrogen sources were screened for production of cell mass with the result that yeast extract was capable of supporting high levels of cell mass. Initial expression studies revealed that a low level of uninduced expression in glycerol-grown BLR 3 fermentations, and stricter dependence of expression upon IPTG induction in clones of HMS174. Consequently, HMS174 was selected for further development. Results of ensuing studies indicated that the bulk of the IPTG-induced expression was located in inclusion bodies (the insoluble fraction). A large fraction of the RiVax™ remained insoluble after lysis in the presence of 3 M urea at pH 7.1. In subsequent experiments, the inducer concentration was reduced to 0.75 mM and 0.25 mM from 1.0 mM. By reducing the IPTG concentration, a significant portion of the expressed protein was in the soluble fraction. The yields in the soluble fraction as measured on a cation exchange column ranged between 1.2 g/L and 1.8 g/L in the soluble fraction.

The purification process comprises capture chromatography using cation exchange resin, endotoxin removal using a charged filter followed by hydrophobic interaction chromatography (HIC) and finally ultrafiltration/diafiltration (UF/DF) to affect buffer exchange in the final formulation for storage of bulk protein. The processing steps include Poros® HS50 Chromatography, Endotoxin Removal by Mustang® E Filtration, Butyl-S Sepharose® 6 FF Chromatography and Final Ultrafiltration/Diafiltration to obtain the final drug substance in 50% w/w glycerol.

Three 100 L fermentations were executed to document this process for process development, one of them as a non-clinical GLP process. These batches were labeled 100 L Run #1 (batch 190-100L-SS-0511-05), 100 L Run #2 (batch 190-1001-FF-0801-05) and the GLP batch (190-100-GLP-FF-090105). Essentially the same results were obtained as with the 10 L fermentations, with slightly lower yields of protein in the soluble fraction. These runs were conducted as process development runs, prior to transferring the methodology to manufacturing, which was carried out in a separate facility.

From analysis of the reverse phase and size exclusion HPLC data and spectral data from protein obtained from 100 L process development runs stored in 50% glycerol at −20° C. for 3 months, it was concluded that the protein stored under these conditions retained native configuration, and there was no evidence of degradation of protein profiles using two different HPLC methods (reverse phase and size exclusion HPLC) or SDS gel electrophoresis. Consequently, three subsequent lots were produced: two engineering run lots and one cGMP lot at the 100 L fermentation scale.

The tangential flow filtrate (TFF) permeate from cell lysis was chromatographed with Poros® HS50. Poros® HS50 chromatography was performed using a K'40 chromatography skid 4. For lot 190-0306-005 the elution product was collected from 0.1 OD A280 on the ascending slope to 0.06 OD $A_{280}$ on the descending slope of the peak. The product from the Poros® HS column was pumped through a Pall Mustang® E filter to remove endotoxin. The Mustang® filtered pool was stored for 2 hours at 2-8° C. prior to the Butyl S chromatography. The filtered Poros® HS50 pool was conditioned by the addition of 3.6 L of 25 mM sodium phosphate, 0.6 M NaCl, 3.0 M Ammonium Sulfate, pH 6.5 and 2.5 L of 25 mM sodium phosphate, 4.0 M NaCl, 0.5 M Ammonium Sulfate, pH 6.5. The conditioned Butyl load had a conductivity of 151 mS/cm. The Butyl S purification was performed using a K'40 chromatography skid. For lot 190-0306-005, the pre-elution eluate from 0.1 OD $A_{280}$ to 0.725 OD $A_{280}$ was collected as I L fractions in 2 L PETG bottles. The eluate, from 0.725 OD $A_{280}$ on the ascending slope to 0.03 OD $A_{280}$ on the descending slope, was collected in the elution media bag. Following the Butyl chromatography, the six fractions were combined with the elution product pool, total=11.4 L. The combined product was diluted 1:1 with formulation buffer (17 mM Histidine, 238 mM NaCl, 15% Glycerol, pH 6.0). The concentration/diafiltration was performed immediately following the dilution. The cGMP batch was released for clinical evaluation and final formulation with Alhydrogel® adjuvant. In summary, a robust and scalable process with an overall yield of approximately 3-5 g of purified protein from 100 L fermentations, with reproducible batch yield. The fermentation yield has been calculated to be in the order of 700-1000 mgs of soluble protein per L of lysate.

Example II: Assessment of RiVax™ Stability Over Time

A formal stability study was conducted over two years on RiVax™ protein from a former engineering run. The assay methodology and criteria for stability were based on the initial set of release specs established for the bulk protein during the first cGMP runs, Characterization tests have included generation of fluorescence spectra on the bulk protein, circular dichroism with thermal melt data, electrospray mass spectrometry, and N-terminal peptide sequencing. CD and fluorescence spectra are being more generally used for investigation into the process of monitoring protein configuration. The evaluation of stability was conducted at 2-4° C., 4° C., and 40°. For protein stored at −20° C. or 2-4° C., there is little evidence of structural change, or the appearance of alternate species over two years (Table 1). A double minima (208 and 222 nm) was observed in the CD spectra of the −20 and 2-8° C. stability samples buffer at all times tested up to 24 months, suggesting retention of significant α-helical character characteristic of T=0 (data not shown). The 40° C. sample displays virtually no negative ellipticity (data not shown). Sampling after the termination of the formal stability study indicated little evidence of gross structural changes. MALDI TOF analysis conducted in 2012 indicated little evidence of deamidated or oxidized peptide species.

TABLE 1

24 months stability of RTA (reference batch) in 50% glycerol at −20° C.

| | TIME (months) | | | | | | | | |
|---|---|---|---|---|---|---|---|---|---|
| Assay | 0 | 1 | 2 | 3 | 6 | 9 | 12 | 18 | 24 |
| Protein concentration, mg/mL | | | | | | | | | |
| O.D. 280 | 0.322 | 0.287 | 0.316 | 0.353 | 0.303 | 0.307 | 0.304 | 0.330 | 0.330 |
| Purity RP HPLC | | | | | | | | | |
| Major peak area (% of T = 0) | 100 | 107 | 105 | 106 | 106 | 94 | 89 | 99 | 103 |
| major peak, % | 96 | 96 | 94 | 97 | 98 | 99 | 99 | 85 | 91.5 |
| minor peak, % | 4 | 4 | 6 | 3 | 2 | 1 | 1 | 15 | 8.5 |
| SEC HPLC major peak, % | 100 | 100 | 100 | 100 | 100 | 100 | 100 | 100 | 100 |
| SDS Gel | 100 | 100 | 100 | 100 | 100 | 100 | 100 | 100 | 100 |
| Secondary structure | | | | | | | | | |
| CD, min peak, nm† | 208 | 208 | 208 | 208 | 208 | 208 | 208 | 208 | 208 |
| Tertiary Structure | | | | | | | | | |
| Tm, ° C. | 55 | 55 | 55 | 55 | 55 | 55 | 55 | 55 | 55 |
| trp- peak, nm | 326 | 326 | 326 | 326 | 326 | 326 | 327 | 327 | 327 |

These studies indicate that RiVax™ protein in solution is stable for years in aqueous buffer in the presence of 50% glycerol. Consequently, in the new manufacturing campaign, we plan to retain the terminal step to add 50% glycerol to the bulk drug substance, with storage at −20° C., which will be used in subsequent formulations steps.

Example III: Stability of RiVax™ Adsorbed to Aluminum Hydroxide Adjuvant

Studies were initiated to monitor the tertiary structure of RiVax™ on the surface of Aihydrogel® using a fluorescence emission detection method that detects changes in tryptophan peak emission reflecting a change in the local environment of the residues from which water is excluded resulting in a red or blue shift indicative of a change in configuration in that region of the molecule.

Figure 2:
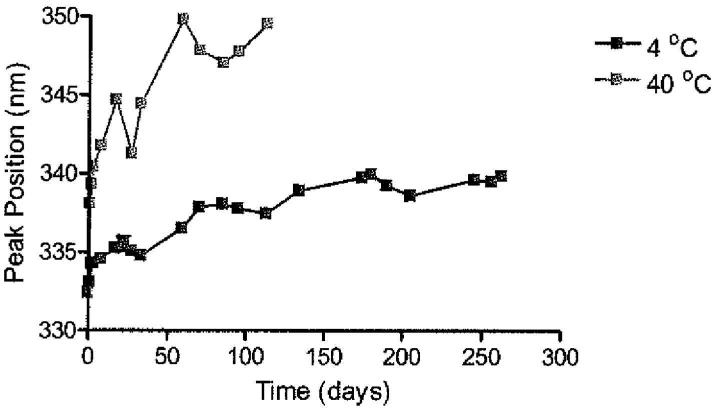
FIG. 2 consists of a representative shift in peak tryptophan fluorescence as a function of time and temperature conditions.

Measurable fluorescence spectra can be detected in vaccine prepared with concentrations of RiVax™ in excess of approximately 50 μg/mL with 0.85 mgs of AlOH. Kinetics of the movement of the peak emission while the protein is adsorbed to Aihydrogel® can be determined using a front face triangular geometry cuvette system. This system is a method to monitor changes of protein configuration under a variety of conditions. For example, the following data have been generated for a reference batch of vaccine stored at 2-4° C. and 40° C. (FIG. 2). Data indicate that the tertiary structure of RiVax™ is significantly changed following incubation of the Alhydrogel®-RiVax™ vaccine at 40° C. for, reflective of a strong red shift and protein unfolding in the environment of the single tryptophan residue in RiVax™. Over 275 days, a gradual red shift of the protein structure occurs, suggesting a slow unfolding of the protein.

Example IV: Manufacture of the Dominant Negative Inhibitor (DNI) for Pre- and Post-Exposure Vaccination The DNI protein was developed as a post-exposure therapeutic. A purification process was developed and cGMP lots were manufactured at the 300-600 Liter fermentation scale. These runs resulted in hundreds of grams of protein that were formulated with excipients to stabilize the protein prior to vaccine formulation and combination.

The protective antigen (PA) gene of *Bacillus anthracis* was cloned into *E. coli* BL21 (DE3) using a pET22-b(+) vector (Novagen, Inc), and mutated by site directed mutagenesis. The resulting double mutant gene (K397D, D425K) encodes the DNI protein and resides on a 2.3 kb Nde I-Xho I fragment. The 5' end of this fragment contains the 23 amino acid pelB leader sequence, including its cleavage signal, which directs the secretion of the DNI protein to the periplasm. A ten amino acid N-terminal extension lies between the pelB signal cleavage site and a GAA codon (glu) that marks position #1 of the mature 83 kD PA as excreted by *B. anthracis*. This ten amino extension is a cloning artifact derived from pET22 vector sequence and does not affect the function of the active DNI protein since it is located on the 20 kb fragment that is cleaved at the cell surface. Two in-frame STOP codons, TAA TGA, terminate transcription immediately upstream of the 6×His-Tag encoded by the pET22-b(+) vector. The original expression plasmid carried the bla gene encoding resistance to ampicillin. Therefore, this gene construct was recloned into pET24-based vectors encoding the NPT II gene for resistance to kanamycin for periplasmic and cytoplasmic expression of DNI. The DNI gene insert was recovered from the original DNI gene construct from Harvard University Medical School by digestion with Nde I and Xho I. Transformants were characterized by simple restriction analysis and used to purify sufficient plasmid DNA to isolate the Nde I-Xho I fragment containing the DNI gene. In addition to the DNI coding region, this fragment contained the pelB leader sequence and the 10 amino acid N-terminal extension. The Nde I-Xho I fragment was ligated into a pET 24 vector cut with Nde I and Xho I, and the ligation products used to transform *E. coli* BLR (DE3) to kanamycin resistance. Transformants were characterized by simple restriction analysis. The complete amino acid sequence of the DNI protein is shown in Table 2.

TABLE 2

| Amino acid sequence of DNI protein |
|---|
| MDIGINSDPMEVKQENRLLNESESSSQGLLGYYFSDLNFQAPMVVTSSTT |
| GDLSIPSSELENIPSENQYFQSAIWSGFIKVKKSDEYTFATSADNHVTMW |
| VDDQEVINKASNSNKIRLEKGRLYQIKIQYQRENPTEKGLDFKLYWTDSQ |
| NKKEVISSDNLQLPELKQKSSNSRKKRSTSAGPTVPDRDNDGIPDSLEVE |
| GYTVDVKNKRTFLSPWISNIHEKKGLTKYKSSPEKWSTASDPYSDFEKVT |
| GRIDKNVSPEARHPLVAAYPIVHVDMENIILSKNEDQSTQNTDSQTRTIS |
| KNTSTSRTHTSEVHGNAEVHASFFDIGGSVSAGFSNSNSSTVAIDHSLSL |
| AGERTWAETMGLNTADTARLNANIRYVNTGTAPIYNVLPTTSLVLGKNQT |
| LATIKA**D**ENQLSQILAPNNYYPSKNLAPIALNAQ**K**DFSSTPITMNYNQFL |
| ELEKTKQLRLDTDQVYGNIATYNFENGRVRVDTGSNWSEVLPQIQETTAR |
| IIFNGKDLNLVERRIAAVNPSDPLETTKPDMTLKEALKIAFGFNEPNGNL |
| QYQGKDITEFDFNFDQQTSQNIKNQLAELNATNIYTVLDKIKLNAKMNIL |
| IRDKRFHYDRNNIAVGADESVVKEAHREVINSSTEGLLLNIDKDIRKILS |
| GYIVEIEDTEGLKEVINDRYDMLNISSLRQDGKTFIDFKKYNDKLPLYIS |
| NPNYKVNVYAVTKENTIINPSENGDTSTNGIKKILIFSKKGYEIG |

FIG. 13. Amino acid sequence of DNI PA83 with the locations of the substitutions at 397 (K to D) and 425 (D to K) also noted.

Competent *E. coli* BLR (DE3) cells were obtained from Novagen, Inc. Ligation mixtures were used to transform competent *E. coli* BLR (DE3) cells to construct the recombinant DNI production strain following the procedures described by the manufacturer (Novagen, Inc.). Clones were selected for expression of the correct size protein band on SDS-PAGE gels with Coomassie staining. The fermentation and purification parameters were developed following standard processes. Both batch and fed-batch parameters were analyzed as were combinations of purification resins and combinations in order to maximize yield while maintaining a high level of purity and a low level of endotoxin, host cell protein (HCP) and DNA contamination. The DNI Drug Substance is an 83 kd protein consisting of 745 amino acids. There are no disulfide bonds present in the full length protein. The full length DNI protein is not capable of having a quaternary structure. However, once DNI is cleaved by furin, the resulting 63 kd protein forms either monomeric heptamers or hetero-heptamers with wt PA. The DNI protein is expressed in the periplasm of *E coli* after induction with IPTG. The product is susceptible to degradation by a neutral protease and the inclusion of EDTA in the buffers during processing seems to limit proteolysis. The cells are cultured in a medium that contains glycerol as a carbon source and Casamino Acids as the principal complex nitrogen source. A completely vegan carbon source was initially used, but a significant amount of uninduced product expression was seen with these reagents. The use of Casamino Acids as the complex nitrogen source prohibits leaky expression of the product prior to induction and results in extracts with limited DNI degradation. The fermentation is performed in a fed-batch mode with a simple linear feeding protocol. The fermentor is inoculated with a seed culture with a temperature shift from 38° C. to 30° C. for induction. The culture is induced with IPTG one hour after the temperature shift. After the culture reaches an OD600 of 10, the fermentation is fed glycerol at a designated feed rate. When the culture attains an OD600 of 20, the temperature is shifted 30 rpm, and the culture is harvested by continuous centrifugation. OD600 with IPTG for 4 hours. The fermentor is chilled to 15° C., airflow is discontinued and agitation is set to 50 rpm at 15° C., airflow is discontinued and agitation is set to 50 rpm, and the culture is harvested by continuous centrifugation.

Although DNI is expressed in the periplasm of *E coli* after induction with IPTG, osmotic shock procedures at large scale are problematic and not reproducible. In addition, there is considerable cell lysis during the processing. We have opted to lyse the cells by homogenization and to remove the bulk of the cell debris by continuous centrifugation. The concentrate is then further clarified by TFF using hollow fiber membranes, followed by flat sheet 10 kDa membranes to concentrate the permeate and to diafilter against the first column buffer. The rationale for the HFM is to assist in improving the quality of the DNI collected in the permeate by reducing impurities that would further tax the purification scheme.

The downstream purification process for DNI involves the use of three column chromatography steps, a Mustang® filtration step and two UF/DF steps. Capture of DNI is achieved by Q Sepharose® FF chromatography. The fractions collected from the Q eluate are pooled based on in-process analysis by SDS-PAGE and passed through a Mustang® filter. The Mustang® filtered Q eluate pool is then diafiltered into phosphate buffer prior to loading onto a ceramic hydroxyapatite (CHT) column. Fractions collected from the CHT eluate are pooled based on in-process analysis by SDS-PAGE. The CHT eluate pool is adjusted to the appropriate ammonium sulfate concentration by dilution, filtered, and loaded onto the Phenyl Sepharose® HP column for final polishing and fractions are collected and pooled based on purity by SDS-PAGE. Final diafiltration into formulation buffer is performed on the Phenyl eluate pool. The formulated bulk is aseptically filtered using a Millipak® 0.2 μm filter and stored in 1000 ml Nalgene® Teflon, PFA Narrow Mouth Bottles at −70° C.

Example V. Formulation of DNI as a Dried Product for Reconstitution

The DNI Drug Product has been formulated using only mannitol and sucrose as excipients and disodium hydrogen phosphate as a buffer. Table 3 lists the quantitative composition of the DNI Drug Product. The bulk drug substance is thawed under 2-8° C. conditions prior to formulation. A 20 mM disodium hydrogen phosphate solution is formulated with disodium hydrogen phosphate and water. The solution is adjusted to a pH of 8.4-8.5. The calculated amounts of mannitol and sucrose are added to the bulk drug substance and mixed until in solution. The solution is adjusted to a pH of 8.1-8.5. Table 4 lists additional elements for inclusion into various emulsion formulation embodiments.

TABLE 3

| Quantitative Composition of the DNI Drug Product | | |
|---|---|---|
| Active Ingredients: | Quantity: | Function: |
| Dominant Negative Inhibitor (DNI) | 25 mg | Drug Substance |
| Inactive Ingredients: | | |
| Mannitol, USP | 113 mg | Excipient |
| Sucrose, USP | 33 mg | Excipient |
| Disodium hydrogen phosphate (Na2HPO4) | 2.4 mg | Buffer |

TABLE 4

| Animal and Non-Animal Derived Stable Emulsion Formulations | |
|---|---|
| SE Formulation Components | |
| SE (animal derived sources) | SE (non-animal derived sources) |
| Squalene (Shark) | Squalene (Olive) |
| Phosphatidylcholine (Egg) | Phosphatidylcholine (Soy 95%) |

TABLE 4-continued

| Animal and Non-Animal Derived Stable Emulsion Formulations | |
|---|---|
| Additional formulation excipients (all non-animal derived) | |
| Glycerol | Glycerol |
| Ammonium Phosphate | Ammonium Phosphate |
| Vitamin E | Vitamin E |
| Pluronic F-68 | Pluronic F-68 |
| Water for Injection | Water for Injection |

Example VI: Formulation of DNI for Vaccination

The loss of potency of rPA vaccine adsorbed to aluminum adjuvants has been a persistent problem encountered during the advanced development of 3rd generation anthrax vaccines and is noted in the recent literature by a loss of capacity of rPA vaccine to induce toxin neutralizing antibodies, the key correlate of protective immunity (Wagner, Verma, et al., 2012, Structural and immunological analysis of anthrax recombinant protective antigen adsorbed to aluminum hydroxide adjuvant, *Clin Vaccine Immunol*, v 19:1465-73). The limitations in recombinant anthrax vaccine development have included rapid loss of potency and effectiveness due to in part to chemical alterations in the rPA protein and subsequent alterations in conformation, limiting the clinical development of purified rPA vaccines. The exact pathways of degradation of rPA vaccine have not been thoroughly characterized, but the large number of asparagine residues has led to the hypothesis that deamidation occurring over time in aqueous buffers can affect protein unfolding and epitope structure and lead to loss of potency and efficacy (Powell, Enama, et al., 2007, Multiple asparagine deamidation of *Bacillus anthracis* protective antigen causes charge isoforms whose complexity correlates with reduced biological activity, *Proteins*, v 68:458-79). The anthrax DNI is an analog of rPA containing two mutations that prevent pore formation and translocation of the holotoxin in the cytosol (Sellman, Mourez and Collier, 2001, Dominant-negative mutants of a toxin subunit: an approach to therapy of anthrax, *Science*, v 292:695-7). DNI binds to the same cell-surface receptors with the same affinity as PA and can form self-assembled heptamers on the surface of cells. The absence of the translocation step prevents DNI-dependent transport of Edema Factor and/or Lethal Factor into cell cytoplasm. Hence, complexes of DNI with LF or EF are nontoxic. DNI was originally proposed for use as an intravenous agent for post-aerosol exposure to anthrax spores to block holotoxin, since one subunit of DNI could block PA-dependent pore formation after heptamerization. It has been shown that animals vaccinated with the DNI antigen induced higher levels of antibodies to toxin and maintained high levels of protective antibody titers for up to one year without booster injections of antigen (Aulinger, Roehrl, et al., 2005, Combining anthrax vaccine and therapy: a dominant-negative inhibitor of anthrax toxin is also a potent and safe immunogen for vaccines, *Infection and Immunity*, v 73:3408-14). The hyperimmunogencity of DNI has been attributed to the defects in pore formation which may enable more efficient antigen presentation in the context of class II MHC. The anthrax DNI is an analog of rPA containing two mutations that prevent pore formation and translocation of the holotoxin in the cytosol. The DNI protein has been produced at scale as a native protein in *E. coli* fermentation and a complete battery of release and process control tests has been implemented during its manufacture. In these studies, the effect of synthetic lipid A TLR-4 agonist Glycopyranoside Lipid A (GLA), an analogue of monophosphoryl Lipid A (MPLa), been studied in lyophilized and liquid adsorbed vaccines. The DNI vaccine candidate was formulated in a 9.5 w/v % trehalose 10 mM ammonium acetate buffer pH 7. Aluminum hydroxide adjuvant (Alhydrogel®) and aluminum hydroxide with GLA were co-formulated as adjuvants. Lyophilized vaccines were stored at 40° C. for 0, 1, 4, 8, and 16 weeks for immunogenicity studies and also at 70° C. for structural studies. Vaccines were lyophilized to increase their stability at high temperature storage. Liquid vaccines of the same formulations were stored at 40° C. for 0 or 8 weeks.

Example VII: Structural Stability Studies

Figure 3:
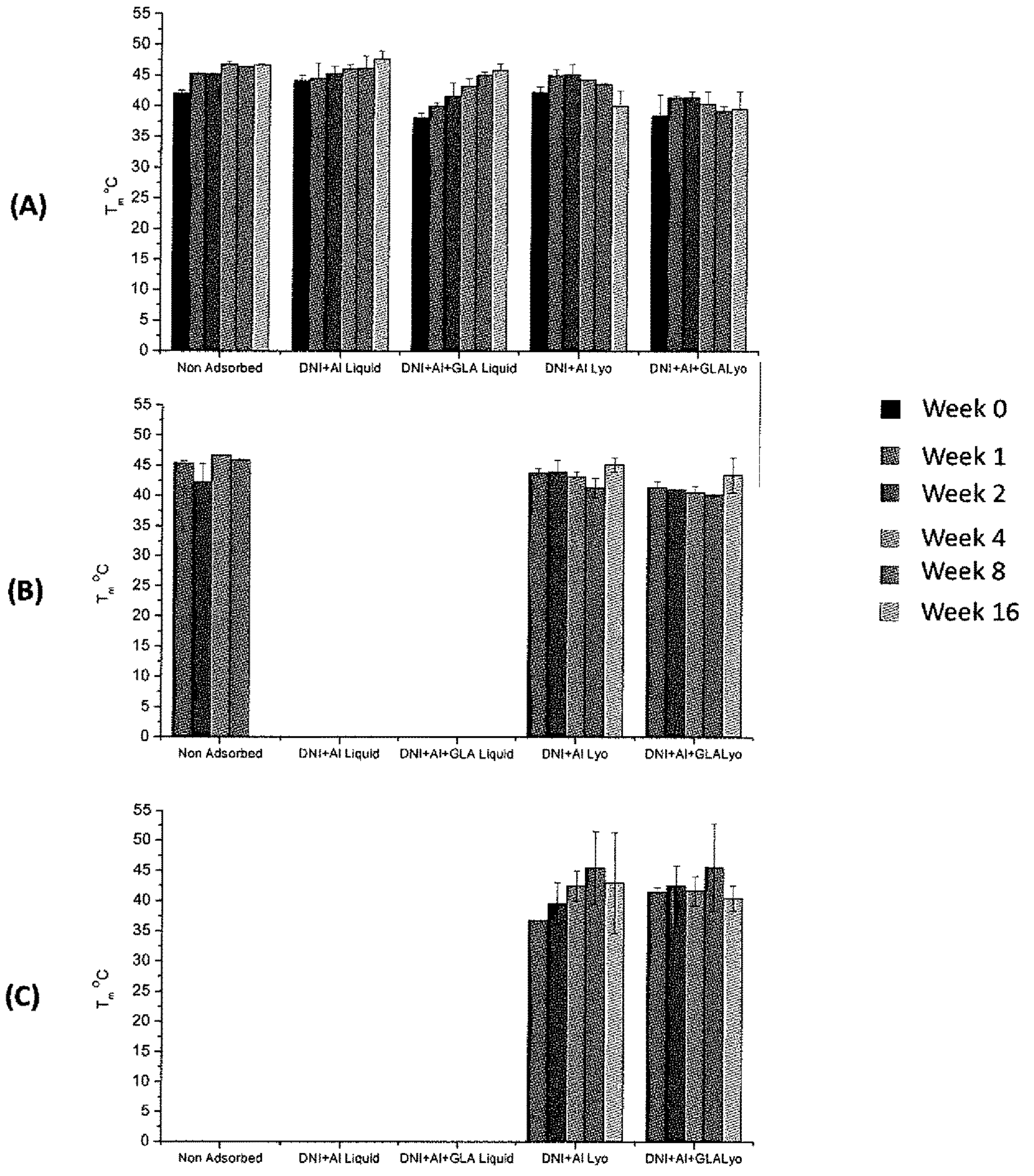
FIG. 3 shows intrinsic fluorescence peak position at the center of mass as a function of temperature for the DNI samples incubated at 4° C. (A), 40° C. (B) and 70° C. (C) for 16 week. Bars are average Tm values for fluorescence peak position of duplicate runs and error bars are standard deviation of mean.

A study was carried out to test the potential use of lyophilized DNI as a stable vaccine after long-term storage and at extremes of temperature. Physical characterization was carried out for lyophilized and liquid formulations of DNI adsorbed on Alhydrogel® and a mixture of Alhydrogel® GLA along with a non-adsorbed liquid DNI. The samples were incubated at 4, 40 and 70° C. and sampled at 1, 2, 4, 8, and 16 weeks. The conformational changes in DNI were analyzed by measuring intrinsic tryptophan fluorescence (FIG. 3). The transition temperatures (Tm) were calculated using the second-order derivative of the peak position or SYPRO® orange fluorescence intensity vs. temperature data. When incubated at the higher temperatures, no transitions were observed in the liquid adsorbed formulations of DNI. This indicates aggregation and/or extensive degradation of protein at higher temperatures. Melting temperatures (Tm) of the samples which showed transition were calculated. Tm values of ~40-45° C. were obtained for all samples incubated at 4° C. No change in the melting temperature was observed with increases in the incubation time. This suggests stability of all formulations at 4° C. The liquid adsorbed formulations did not show any transitions at 40 and 70° C. and therefore Tm was not calculated. For non-adsorbed samples, a Tm value of ~42-45° C. was calculated for samples incubated at 40° C. for 1, 2, 4 and 8 weeks. As mentioned previously, samples incubated for 16 week at 40° ° C. and the entire study period at 70° C. did not show any transition and Tm could not be calculated. In the case of lyophilized samples Tm values of ~40-45° C. were obtained for all the samples incubated at 4, 40 and 70° C. for 16 weeks. This suggests much improved conformational stability of lyophilized formulation.

Example VIII: Additional Characterization Studies with Lyophilized DNI Vaccine: Particle Size, Glass Transition Temperature, and Adsorption/Desorption Studies Lyophilized vaccines were characterized for glass transition temperature, protein adsorption, and particle size. The onset glass transition temperature was found to be 115.5° C.±1.6 for lyophilized Alhydrogel® vaccine formulations and 117.3° C.±3.8 for lyophilized Alhydrogel®/GLA formulations. Both formulations have high glass transition temperatures similar to pure trehalose, showing minimal water in the lyophilized cakes.

Example IX: Antibody Responses and Temperature Stability of Lyophilized Adsorbed DNI Vaccine Immunogenicity of the liquid and lyophilized vaccines was tested in Balb/c mice at a single dose level of 10 μg per mouse with serological endpoints of total antibodies by anti-PA ELISA (Table 5) and TNA (Table 6). Mice were vaccinated with 10 μg DNI dose s.c. on days 0 and 14 and were bled for serum analysis on days 0, 14 and 28. Neutralizing titers (FIG. 4) remained constant over the storage time and anti-DNI antibody titers only showed a slight decrease for the Alhydrogel®/GLA vaccines at longer storage time points. Vaccines containing Alhydrogel®+GLA produced a more robust immune response than vaccines containing only Alhydrogel® adjuvant, indicating the potential for a vaccine administered with fewer doses if GLA is included in the formulation.

TABLE 5

ELISA responses in Balb/c mice immunized (2x) with DNI vaccine adsorbed to AlOH (10 μg)

| | DNI unformulated | DNI adsorbed (liquid) | DNI adsorbed (liquid) TLR-4 | DNI-adsorbed lyophilized | DNI adsorbed lyophilized TLR-4 |
|---|---|---|---|---|---|
| 1° (day 14) | | | | | |
| Seroconversion rate (>1:1000) | 0/10 | 3/10 | 8/9 | 2/10 | 8/9 |
| GMT | — | 69 | 8469 | 12 | 4704 |
| Range | — | 1-3,492 | 176-63,404 | 1-1,985 | 1-102,000 |
| 2° (day 28) | | | | | |
| Seroconversion rate (>1:100,000) | 0/10 | 4/10 | 9/9 | 5/10 | 10/10 |
| GMT | 1.6 | 72,448 | 1,433,709 | 66,194 | 1,057,664 |
| Range | 1-200 | 7,112-1,329,414 | 347,709-7,309,677 | 9,224-291,047 | 115,858-15,015,281 |

TABLE 6

| TNA responses in Balb/c mice immunized (2x) with DNI vaccine | | | | | |
|---|---|---|---|---|---|
| | DNI unformulated | DNI adsorbed (liquid) | DNI adsorbed (liquid) TLR-4 | DNI-adsorbed lyophilized | DNI adsorbed lyophilized TLR-4 |
| 2° (day 28) | | | | | |
| Seroconversion rate (>1:100) | 0/10 | 8/10 | 9/9 | 8/10 | 10/10 |
| GMT | — | 79 | 503 | 60 | 324 |
| Range | — | 1-400 | 400-1,600 | 1-400 | 100-1,600 |

Figure 4:
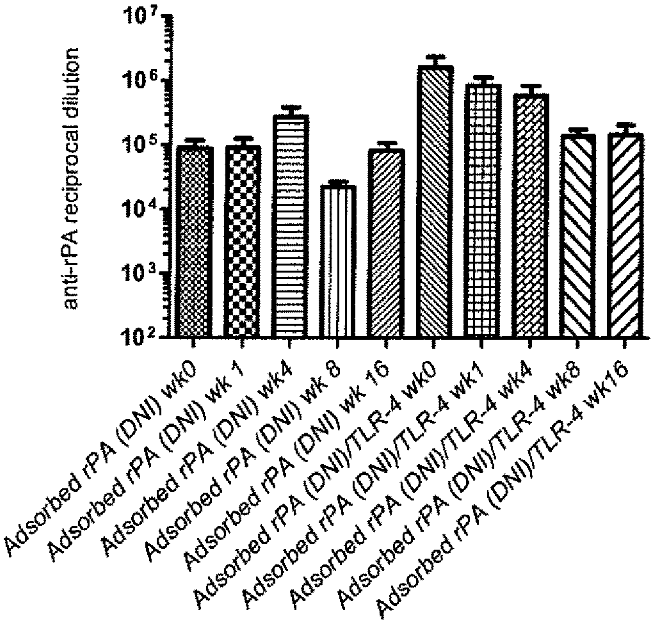
FIG. 4 depicts reciprocal anti-DNI antibody (A) and neutralizing (B) titers of liquid and lyophilized vaccines without any high temperature storage and with 1, 4, 8 and 16 weeks of storage at 40° C.
Figure 4:
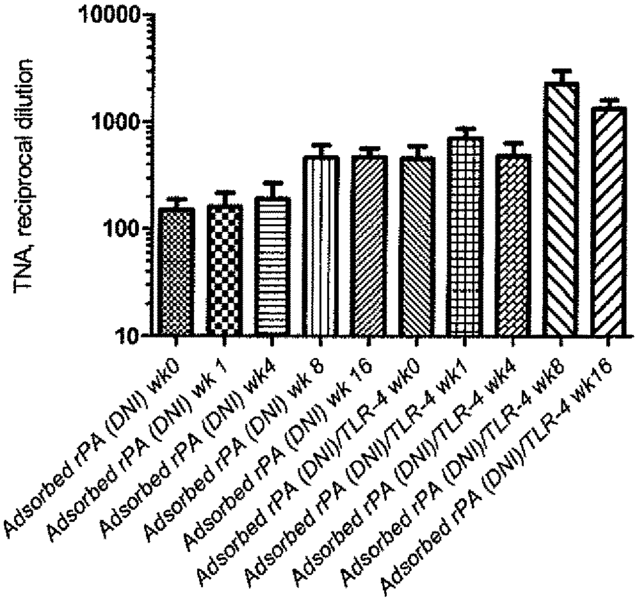

Newly made liquid (T=0) and lyophilized vaccines produced equivalent immune responses demonstrating that lyophilization does not decrease the immunogenicity of the vaccine. Lyophilized vaccines remained immunogenic even after being stored at 40° C. for 16 weeks. When synthetic MPL is added to the lyophilized formulations during processing, the resulting lyophilized DNI vaccine generated robust immune responses and elicited neutralizing antibodies that are enhanced in relationship to the vaccine that does not contain the synthetic TLR-4 agonist GLA (Tables 3 and 4). The TNA titers after 2 vaccinations with GLA TLR-4 lyophilized as well as liquid vaccine not exposed to temperature stress were 5 to 10-fold higher than in sera from mice vaccinated with the corresponding Alhydrogel® vaccines. Furthermore, even when the vaccines were stored at 40° C. for up to 16 weeks prior to administration of the vaccines, there was no evident loss of TNA (FIG. 4). The lyophilized DNI vaccine that was made with synthetic MPL (GLA) was also stable at 40° C. for at least 16 weeks, indicating that the synthetic adjuvant component was stabilized by the glassification process in contrast to liquid suspension vaccines held at 4° C. for 8 weeks which had significantly decayed (not shown).

Example X: DNI/GLA-SE Induces High Titer Toxin Neutralizing Antibodies

Figure 5:
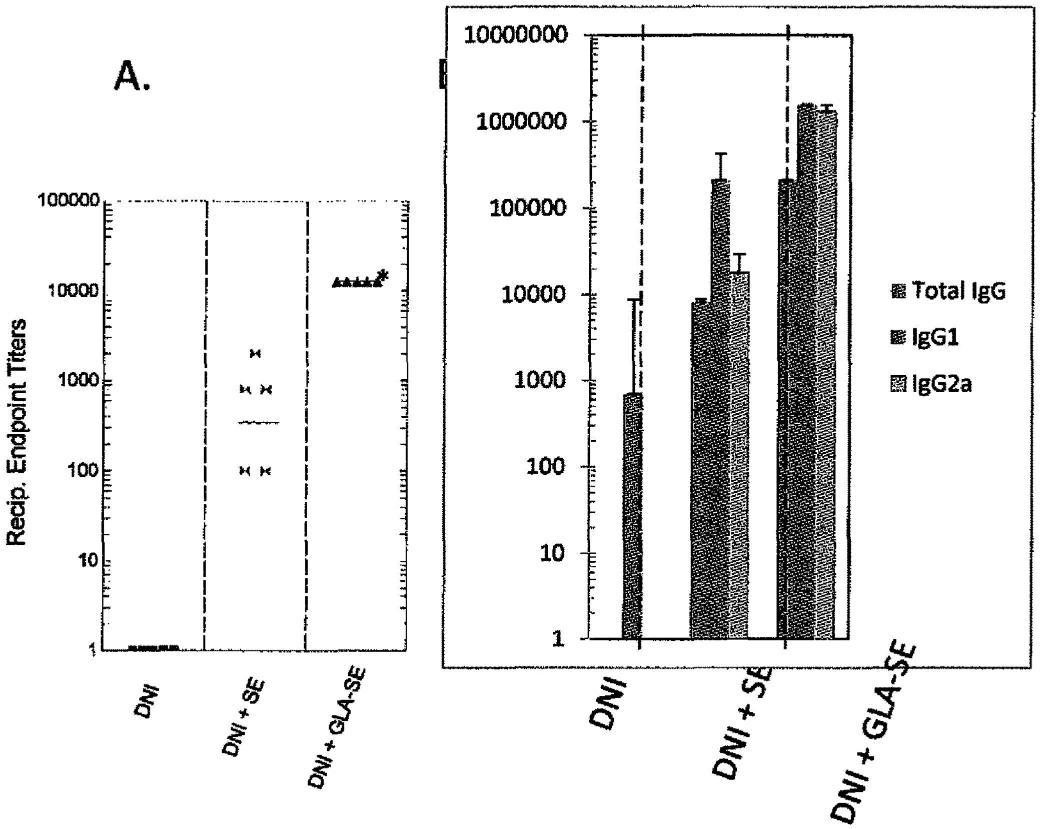
FIG. 5 shows 7 week old Balb/c mice immunized by s.c. injection on days 0 and day 21 with 5 μg of DNI protein in PBS (DNI), SE (DNI+SE) or GLA/SE (DNI+GLA-SE). Serum TNA (A) or total ELISA reactive IgG1, IgG, and IgG2a antibodies (B) were determined on day 28 and expressed as reciprocal endpoint titers. *Titers were in excess of 1:12,800.

To evaluate the effect of GLA-SE in conjunction with DNI, Balb/C mice were vaccinated with 5 micrograms of DNI admixed with SE-GLA. SE, or with buffer alone (FIG. 5). Anti-rPA serum titers were determined in serum collected one week after the second vaccination and antibody titers measured by ELISA and neutralizing antibodies were determined by TNA. In the case of both SE and GLA-SE, there was a skewing of the antibody responses towards IgG2a, indicative of admixed Th1/Th2 response and the generation of antibodies that are associated with Fcγ component of anthrax toxin neutralization. Vaccination with the DNI protein alone resulted in negligible IgG2a. Interestingly, the SE-GLA vaccine induced the highest titers of toxin neutralizing antibodies (1:12,800) in contrast to mice that were immunized with protein alone that did not develop measurable neutralizing antibodies.

Example XI: Combination Vaccine Testing

Groups of ten female Balb/c mice (Jackson Laboratories, Bar Harbor, Me.) with 10 μg of either: RiVax™, DNI, or a combination of the two, in the presence of the adjuvant Alum (0.85 mg/mL) in PBS. A control group received Alum only (Table 7). Lyophilized dominant negative inhibitor (DNI) was manufactured by Baxter Pharmaceutical Solutions LLC (Bloomington, Ind.). It was stored for 8 years at 4° C. (date of manufacture: Dec. 15, 2003, batch number: 803918A). On the day of use, the lyophilized powder was reconstituted in sterile water. RiVax™ (lot 190-100L-GLP-FF-090105) and aluminum hydroxide (Alhydrogel®) were provided by Soligenix, Inc. (Princeton, N.J.). Alum was provided in histidine buffer (10 mM histidine, 144 mM NaCl, pH 6.0), while RiVax™ was in 50% glycerol, 50% histidine buffer. All mouse experiments were approved by the Wadsworth Center's Institutional Animal Care and Use Committee (IACUC).

TABLE 7

| Combination Vaccine Testing Results | | | | | | | | | | | |
|---|---|---|---|---|---|---|---|---|---|---|---|
| | | Ricin Endpoint | | PA Endpoint | | Ricin Neutralizing | | LT Neutralizing | | Survival | |
| Group[c] | Mouse | Day 20 | Day 200 | Day 20 | Day 200 | Day 20 | Day 200 | Day 20 | Day 200 | Ricin | LT |
| 1A | 1 | 204800 | 102400 | 1 | 1 | 1 | 800 | 1 | 1 | | No |
| | 2 | 204800 | 204800 | 1 | 1 | 1 | 1600 | 1 | 1 | | No |
| | 3 | 204800 | 102400 | 1 | 1 | 1 | 800 | 1 | 1 | | No |
| | 4 | 204800 | 51200 | 1 | 1 | 100 | 100 | 1 | 1 | | No |
| | 5 | 204800 | 102400 | 1 | 1 | 1 | 400 | 1 | 1 | | No |
| 1B | 1 | 204800 | 51200 | 1 | 1 | 1 | 100 | 1 | 1 | Yes | |
| | 2 | 204800 | 102400 | 1 | 1 | 1 | 800 | 1 | 1 | Yes | |
| | 3 | 204800 | 102400 | 1 | 1 | 1 | 200 | 1 | 1 | Yes | |
| | 4 | 204800 | 204800 | 1 | 1 | 1 | 1600 | 1 | 1 | Yes | |
| | 5 | 204800 | 204800 | 1 | 1 | 1 | 400 | 1 | 1 | Yes | |
| 2A | 1 | 1 | 1 | 204800 | 409600 | 1 | 1 | 1600 | 3200 | No[a] | Yes |
| | 2 | 1 | 1 | 204800 | 204800 | 1 | 1 | 800 | 800 | No[a] | Yes |
| | 3 | 1 | 1 | 204800 | 204800 | 1 | 1 | 800 | 1600 | No[a] | Yes |
| | 4 | 1 | 1 | 204800 | 102400 | 1 | 1 | 1600 | 1600 | No[a] | Yes |
| | 5 | 1 | 1 | 204800 | 102400 | 1 | 1 | 1600 | 1600 | No[a] | Yes |
| 2B | 1 | 1 | 1 | 102400 | 204800 | 1 | 1 | 200 | 1600 | No | |
| | 2 | 1 | 1 | 204800 | 204800 | 1 | 1 | 800 | 3200 | No | |

TABLE 7-continued

| Combination Vaccine Testing Results | | | | | | | | | | | |
|---|---|---|---|---|---|---|---|---|---|---|---|
| | | Ricin Endpoint | | PA Endpoint | | Ricin Neutralizing | | LT Neutralizing | | Survival | |
| Group[c] | Mouse | Day 20 | Day 200 | Day 20 | Day 200 | Day 20 | Day 200 | Day 20 | Day 200 | Ricin | LT |
| | 3 | 1 | 1 | 204800 | 102400 | 1 | 1 | 1600 | 1600 | No | |
| | 4 | 1 | 1 | 204800 | 204800 | 1 | 1 | 3200 | 1600 | No | |
| | 5[b] | | | | | | | | | | |
| 3A | 1 | 51200 | 102400 | 102400 | 51200 | 1 | 800 | 400 | 800 | Yes[a] | Yes |
| | 2 | 204800 | 102400 | 204800 | 51200 | 1 | 800 | 800 | 800 | Yes[a] | Yes |
| | 3 | 204800 | 204800 | 102400 | 51200 | 1 | 800 | 100 | 200 | | No |
| | 4 | 102400 | 204800 | 6400 | 51200 | 1 | 800 | 200 | 1600 | Yes[a] | Yes |
| | 5 | 102400 | 51200 | 51200 | 51200 | 1 | 400 | 200 | 400 | Yes[a] | Yes |
| 3B | 1 | 102400 | 102400 | 25600 | 51200 | 1 | 400 | 1 | 400 | Yes | |
| | 2 | 102400 | 51200 | 12800 | 102400 | 1 | 100 | 400 | 1600 | Yes | |
| | 3 | 204800 | 102400 | 204800 | 102400 | 1 | 400 | 3200 | 800 | Yes | |
| | 4 | 102400 | 51200 | 12800 | 51200 | 1 | 200 | 100 | 1600 | Yes | |
| | 5 | 204800 | 102400 | 51200 | 25600 | 1 | 400 | 800 | 1600 | Yes | |
| 4A | 1 | 1 | 1 | 1 | 1 | 1 | 1 | 1 | 1 | | No |
| | 2 | 1 | 1 | 1 | 1 | 1 | 1 | 1 | 1 | | No |
| | 3 | 1 | 1 | 1 | 1 | 1 | 1 | 1 | 1 | | No |
| | 4 | 1 | 1 | 1 | 1 | 1 | 1 | 1 | 1 | | No |
| | 5 | 1 | 1 | 1 | 1 | 1 | 1 | 1 | 1 | | No |
| 4B | 1 | 1 | 1 | 1 | 1 | 1 | 1 | 1 | 1 | No | |
| | 2 | 1 | 1 | 1 | 1 | 1 | 1 | 1 | 1 | No | |
| | 3 | 1 | 1 | 1 | 1 | 1 | 1 | 1 | 1 | No | |
| | 4 | 1 | 1 | 1 | 1 | 1 | 1 | 1 | 1 | No | |
| | 5 | 1 | 1 | 1 | 1 | 1 | 1 | 1 | 1 | No | |

[a]second challenge.

[b]mouse 2B-5 died unexpectedly before blood was collected on day 20.

[c]1 = RiVax ™ alone, 2 = DNI alone, 3 = RiVax ™ + DNI, 4 = Alum only.

Groups labeled with A received lethal toxin in the first challenge, and groups with B received ricin in the first challenge.

Titer set to 1 if there was no detectable titer.

Each antigen was mixed with aluminum hydroxide and allowed to adsorb while rotating at 4° C. for 3 hours prior to immunization. Antigens in dual immunizations were adsorbed to Alum separately and mixed before injection. Mice were given a prime immunization, 400 uL i.p., and a boost 2 weeks later. Their immune response was characterized 1 week after the boost, and again 6 months later, by collecting blood from the tail vein.

ELISAs for determining endpoint titers were performed. Plastic plates were coated with either ricin or PA, the blocked with 2% goat serum. Immune serum was then serially diluted two-fold across the plate in duplicate. Secondary antibody detected bound murine-IgG, was visualized by the HRP/TMB calorimetric reaction, and absorbance was detected at 450 nm on a VersaMax® spectrophotometer (Molecular Devices, Sunnyvale, Calif.). Endpoint titer was defined as the highest dilution at which the absorbance was still higher than 3 times the background absorbance. On day twenty, six days after boost, anti-ricin titers in the ten mice given RiVax™ alone were very high, with a geometric mean inverse titer of 204,800. At the same time point, mice given DNI alone also had very high anti-PA titers, with a geometric mean of 187,802. Neither of these groups had any detectable titers against the opposite antigen (Table 8).

TABLE 8

| Geometric Mean Endpoint Titers[a] | | | | |
|---|---|---|---|---|
| | Anti-Ricin | | Anti-PA | |
| | Day 20 | Day 200 | Day 20 | Day 200 |
| RiVax ™ | 204800 | 109750 | 1 | 1 |
| DNI | 1 | 1 | 187802 | 175564 |

TABLE 8-continued

| Geometric Mean Endpoint Titers[a] | | | | |
|---|---|---|---|---|
| | Anti-Ricin | | Anti-PA | |
| | Day 20 | Day 200 | Day 20 | Day 200 |
| RiVax ™ + DNI | 126069 | 95543 | 40637 | 54875 |

[a]when no titers are detectable, the titer is assigned as 1 for geometric mean calculation Mice that received the dual immunization with 10 µg of each antigen had high titers against both antigens, although the absolute levels were around half of the mice given each antigen by itself. Anti-ricin titers in this group had a geometric mean of 126,069, while anti-PA titers had a geometric mean of 95,543. Therefore, at the endpoint titer level, there is clearly some immune interference from each antigen that impairs the response to the opposite antigen.

Each sample was also tested for neutralizing titers against ricin, in a Vero cell cytotoxicity assay, and lethal toxin, in a J774 cell assay (Tables 9 and 10). Neutralizing titers were defined as the highest dilution in which at least 50% of the cells were protected from the toxin, as defined by the live and toxin killed control wells. Vero cell assays utilized 10 ng/mL of ricin toxin, whereas J774 assays employed 300 ng/mL lethal toxin, with a 1:1 mass ratio of PA and LF. In both assays, 5,000 cells per well were seeded in a 96 well opaque cell culture treated plate in DMEM plus 10% FBS. Immune serum was mixed with toxin at a 1:100 serum dilution, and diluted 2 fold into toxin containing media. In Vero cell assays, the toxin/serum mixture was allowed to incubate with cells at 37° C. for 2 hours, at which point the media was changed. Cell Titer Glo® was then used to determine cell viability 48 hours later. In the J774 assay, the media was not changed after toxin/serum mixture addition, and cell viability was determined with Cell Titer Glo® 24 hours later.

TABLE 9

| Geometric Mean Neutralizing Titers of Challenge Groups | | | | | | | | | |
|---|---|---|---|---|---|---|---|---|---|
| | Day 20 - LT[b] | | | Day 200 - LT | | | Day 200 - Ricin[c] | | |
| | Ricin[a] | LT[a] | Total | Ricin | LT | Total | Ricin | LT | Total |
| RiVax | 1 | 1 | 1 | 1 | 1 | 1 | 400 | 528 | 459 |
| DNI | 951 | 1213 | 1074 | 1903 | 1600 | 1745 | 1 | 1 | 1 |
| RiVax + DNI | 159 | 264 | 205 | 1056 | 606 | 800 | 264 | 696 | 429 |

[a]toxin used in particular group;
[b]LT, Lethal Toxin;
[c]very little day 20 ricin neutralizing titers

TABLE 10

| Protection from Toxin Challenges | | | |
|---|---|---|---|
| | 1st Challenge | | 2nd Challenge |
| | Ricin | LT | Ricin |
| RiVax | 5/5 | 0/5 | N/A |
| DNI | 0/4[a] | 5/5 | 0/5 |
| RiVax + DNI | 5/5 | 4/5 | 4/4 |
| Alum Only | 0/5 | 0/5 | N/A |

[a]one mouse died unexpectedly before the first tail bleed;
N/A, no mice to challenge with that toxin in the second challenge

Example XII. Manufacturing of Lyophilized Stabilized Ricin Vaccine

Figure 6:
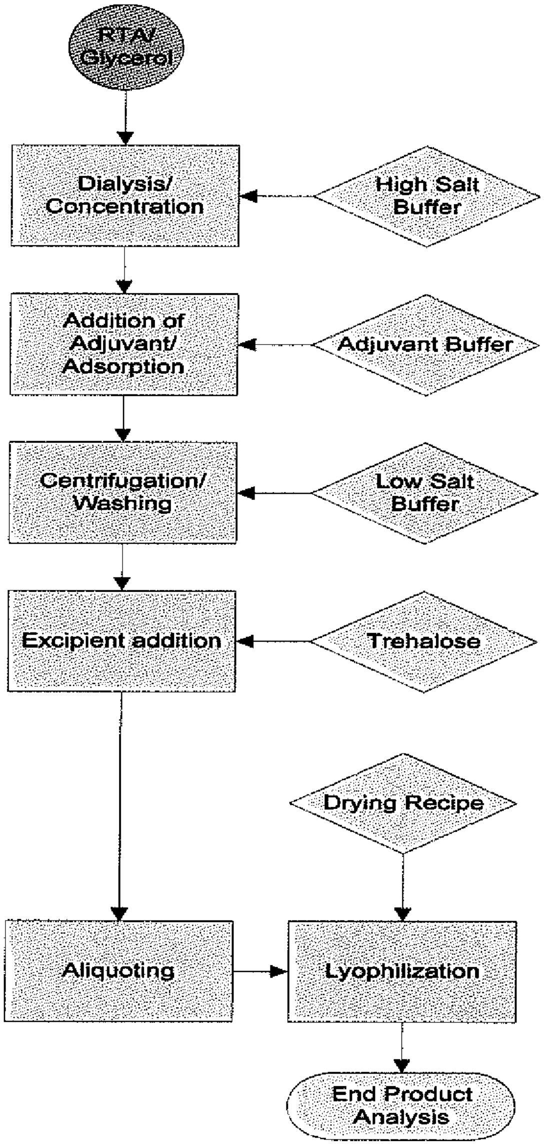
FIG. 6 shows the flow chart for formulating ricin A chain vaccine (RiVax™) in conjunction with aluminum hydroxide adjuvant and subsequent lyophilization.

Colloidal suspensions of aluminum adjuvant particles are unstable and freezing-induced concentration of adjuvant suspensions cause aggregation during freeze-thawing, meaning that conventional lyophilization techniques cannot be successfully applied to vaccines that employ aluminum adjvuants. During lyophilization, aggregation of colloidal aluminum hydroxide suspensions can be inhibited by reducing the extent of their freeze-concentration by using formulations that contain high concentrations of glass-forming excipients, and by limiting the time over which the freeze-concentration occurs by using formulations that contain high concentrations of glass-forming excipients, as well as limiting the time over which the freeze-concentrated suspensions can aggregate by using rapid cooling procedures to maximize the kinetics of glass formation. This process has been developed from examination of a number of parameters and as outlined in FIG. 6.

1. PROCEDURE

- 1.1. Starting Material Dialysis and Concentration
  - 1.1.1. Prepare Dialysis Buffer (20 mM His mhc, 144 mM NaCl)
    - 1.1.1.1. Dissolve 50.31 g of Histidine monohydrochloride and 101.0 g of NaCl into 12 L of USP water.
    - 1.1.1.2. Adjust the pH of the solution to 6.5 with 1N HCl or NaOH
    - 1.1.1.3. Sterile filter the solution
  - 1.1.2. Slide-A-Lyzer ® Preparation and loading
    - 1.1.2.1. Hydrate a 70 ml Slide-A-Lyzer ® (SLD) for two min in the buffer
    - 1.1.2.2. Remove the top of the device and introduce 45 ml of 50% glycerol RiVax ™ stock protein solution
    - 1.1.2.3. Squeeze the membrane lightly to remove any air from the top of the device and close it with the top.
  - 1.1.3. Dialysis
    - 1.1.3.1. Float the SLD in 4 L of sterile HBS
    - 1.1.3.2. Stir the buffer for 2 h at room temperature to allow to equilibrate
    - 1.1.3.3. After 2 h discard the old buffer and replace it with 4 L of fresh dialysis buffer and stir for another 2 h at RT
    - 1.1.3.4. After stirring in fresh buffer for 2 h at RT replace the buffer one last time and move the beaker to 4° C. and allow to stir at 4° C. overnight.
  - 1.1.4. Repeat 4.1.1-4.1.3 in parallel to prepare twice the amount of starting material
  - 1.1.5. Concentration
    - 1.1.5.1. Remove the dialyzed material from the SLD and measure the final volume and concentration of protein (Pierce 23227).
    - 1.1.5.2. Calculate the final volume of concentrate needed to reach a final concentration of 0.5 mg/ml of protein
    - 1.1.5.3. Concentrate the dialyzed material down to the calculated volume with an Amicon ® ultra centrifugal concentrator
    - 1.1.5.4. Sterile filter the concentrate with a 0.22 um syringe filter to remove any precipitated material
    - 1.1.5.5. Measure the volume and protein concentration of the concentrate (Pierce 23227)

-continued

| 1. PROCEDURE |
|---|
| 1.2. Prepare solutions |
| 1.2.1. Prepare 50 mL 2X histidine buffered saline (2X HBS, histidine; 40 mM, saline; 288 mM) |
| 1.2.1.1. Add 209.64 mg His mhc to 40 ml of WFI dissolve completely. |
| 1.2.1.2. Add 841.5 mg sodium chloride to the solution and dissolve completely. |
| 1.2.1.3. Adjust the solution to pH 6.5 by adding NaOH or HCl solution dropwise. |
| 1.2.1.4. Bring the final volume to 50 mL by adding WFI. |
| 1.2.1.5. Label the flask 2X histidine buffered saline. |
| 1.2.2. Prepare 2X Antigen Solution in 1X HBS |
| 1.2.2.1. From the concentrate normalize the solution to a 0.4 mg/ml solution using 1X histidine buffer as the diluent |
| 1.2.2.2. Verify the concentration of protein (Pierce 23227) and measure the total volume. |
| 1.2.3. Prepare 200 mL Alhydrogel ® solution with 3.4 mgAl/ml in 1X HBS |
| 1.2.3.1. Add 68 ml of 10 mgAl/ml stock Alhydrogel ® to 10 ml of 2X HBS and 3.2 ml of WFI |
| 1.2.4. Prepare 1 L of Histidine Buffer with no sodium chloride (HB) |
| 1.2.4.1. Add 2.094 g of His mhc to 950 ml of WFI and dissolve completely. |
| 1.2.4.2. pH the solution to 6.5 with 1N NaOH |
| 1.2.4.3. Bring the final volume to 1 L by adding WFI |
| 1.2.4.4. Sterile filter the solution |
| 1.2.4.5. Label the flask histidine buffer no saline. |
| 1.2.5. Prepare 200 mL 4X Trehalose in 1X HB. |
| 1.2.5.1. Add 64 g trehalose to 175 ml histidine buffer and dissolve completely. |
| 1.2.5.2. Bring the volume of the final solution to 200 mL by adding 1X HB as needed. |
| 1.2.5.3. Sterile filter the solution |
| 1.2.5.4. Label the flask 4X Trehalose in HB. |
| 1.3. Lyophilizer Preparation |
| 1.3.1. Initialize the cooling system. |
| 1.3.2. Set the condenser to −80° C. |
| 1.3.3. Set the sample shelves to −10° C. |
| 1.3.4. Program the lyophilization parameters found in the automatic program. |
| 1.4. RiVax ™ conjugation |
| 1.4.1. Table 12.4 Ratio of components |

| 4x Alhydrogel ® in 1X HBS | 2X RiVax ™ in 1X HBS | 4X Trehalose in IX HB |
|---|---|---|
| 1 | 2 | 1 |

| |
|---|
| 1.4.2. Mix the Alhydrogel ® and RiVax ™ Components for this run according to table 12.3.1 |
| 1.4.3. Vortex the mixture briefly. |
| 1.4.4. Add a magnetic stir-bar to the flask. |
| 1.4.5. Stir the solutions on the stir plate at 4° C. for 1 h on setting 5. |
| 1.4.6. Assay the mixture for supernatant protein concentration and verify 95% adsorption. |
| 1.5. Washing |
| 1.5.1. Centrifuge the mixture in two 250 ml conical tube on the bench top centrifuge at 3000 rpm for 10 min to pellet the adsorbed adjuvant |
| 1.5.2. Re-suspend the pellet in 450 ml of Histidine Buffer with no salt by pipetting up and down |
| 1.5.3. Centrifuge again at 3000 rpm for 10 min. |
| 1.5.4. Re-suspend the pellet in 2 parts of Histidine buffer(no saline) |
| 1.5.5. After mixing is complete add 1 part 4X Trehalose in 1XHBS. |
| 1.6. Stir for five minutes to mix. |
| 1.7. Aliquot 1 mL conjugated vaccine into 2 ml lyovials and half stopper with slotted stoppers and mark the side of each vial with a permanent marker to distinguish the set |
| 1.8. Aliquot 1 mL WFI into each of 500 lyovials. |
| 1.9. Arrange on the aluminum shelf insert with the dummy vials arranged on the outside of the grouping. |
| 1.10. Insert the aluminum shelf plate with the vial arrangement into the pre-cooled sample shelf. |

-continued

1. PROCEDURE 1.11. Lyophilization 1.11.1. Remove the control program from manual mode and initiate automatic mode with the following drying recipe.

| Product Name | | RiVax ™-TR | | | | |
|---|---|---|---|---|---|---|
| Product Number | | RD13-029 | | | | |
| Operator | | Nanotherapeutics R & D | | | | |
| Freeze | Step | 1 | 2 | | | |
| Shelf Set Point | ° C. | −10 | −40 | | | |
| Ramp Rate | ° C./min | 0 | 0.5 | | | |
| Hold Time | Minutes | 15 | 120 | | | |
| Final Freeze Setpoint | ° C. | −40 | | | | |
| Extra Freeze Time | Minutes | 0 | | | | |
| Starting Vacuum Setpoint | mTorr | 60 | | | | |
| Drying | Step | 1 | 2 | 3 | 4 | 5 |
| Shelf Set Point | ° C. | −40 | −20 | −20 | 0 | 30 |
| Ramp Rate | ° C./min | 0 | 0 | 0 | 0.2 | 0.5 |
| Hold Time | Minutes | 30 | 30 | 1200 | 0 | 300 |
| Vacuum Setpoint | mTorr | 60 | 60 | 60 | 60 | 60 |
| Final | | | | | | |
| Shelf Set Point | ° C. | 24 | | | | |
| Ramp Rate | ° C./min | 0 | | | | |
| Vacuum Setpoint | mTorr | 60 | | | | |
| Total Cycle Time 28 h | | | | | | |

1.12 Back fill the chamber to 0.5 atm with medical nitrogen.

1.13. Stopper the vials with shelf actuation.

1.14. Break the vacuum directly to the atmosphere.

1.15. Apply an aluminum seal to each of the vials.

1.16. Label each vial with RD13-029 a and b respectively along with the date of manufacture 1.17. Store samples at −80° C.

As used in this specification and in the appended claims, the singular forms include the plural forms. For example the terms “a,” “an,” and “the” include plural references unless the content clearly dictates otherwise. Additionally, the term “at least” preceding a series of elements is to be understood as referring to every element in the series. The inventions illustratively described herein can suitably be practiced in the absence of any element or elements, limitation or limitations, not specifically disclosed herein. Thus, for example, the terms “comprising,” “including,” “containing,” etc. shall be read expansively and without limitation. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the invention claimed. Thus, it should be understood that although the present invention has been specifically disclosed by preferred embodiments and optional features, modification and variation of the inventions herein disclosed can be resorted by those skilled in the art, and that such modifications and variations are considered to be within the scope of the inventions disclosed herein. The inventions have been described broadly and generically herein. Each of the narrower species and subgeneric groupings falling within the scope of the generic disclosure also form part of these inventions. This includes the generic description of each invention with a proviso or negative limitation removing any subject matter from the genus, regardless of whether or not the excised materials specifically resided therein. In addition, where features or aspects of an invention are described in terms of the Markush group, those schooled in the art will recognize that the invention is also thereby described in terms of any individual member or subgroup of members of the Markush group. It is also to be understood that the above description is intended to be illustrative and not restrictive. Many embodiments will be apparent to those of in the art upon reviewing the above description. The scope of the invention should therefore, be determined not with reference to the above description, but should instead be determined with reference to the appended claims, along with the full scope of equivalents to which such claims are entitled. Those skilled in the art will recognize, or will be able to ascertain using no more than routine experimentation, many equivalents to the specific embodiments of the invention described. Such equivalents are intended to be encompassed by the following claims.

The invention claimed is:

1. An immunogenic composition comprising a first antigen comprising a ribosome inactivating protein and a second antigen comprising a toxin derived from bacterial spores, wherein the immunogenic composition is formulated to elicit protective immunity to each of the first and second antigenic components without causing immune interference between the first and the second antigens after administration to an individual, further comprising at least one disaccharide glass forming excipient, aluminum hydroxide, an effective amount of glycopyranoside lipid A, and a buffer consisting of 50% glycerol buffer and 50% histidine buffer.

2. The composition of claim 1, wherein the composition yields a measurable increase in neutralizing antibodies to the first antigen comprising the ribosome inactivating protein.

3. The composition of claim 1, wherein the composition is capable of yielding a measurable increase in neutralizing antibodies to the second antigen comprising a toxin derived from bacterial spores.

4. The composition of claim 1, wherein the composition is capable of yielding a measurable increase in neutralizing antibodies to both the first and the second antigen.

5. The composition of claim 1, wherein the composition elicits a measurable increase in neutralizing antibodies to the first antigen at least 200 days post-administration.

6. The composition of claim 1, wherein the composition elicits a measurable increase in neutralizing antibodies to the second antigen at least 200 days post-administration.

7. The composition of claim 1, wherein the composition elicits a measurable increase in neutralizing antibodies to the first and the second antigen at least 200 days post-administration.

8. The composition of claim 1, further wherein the composition is administered prior to exposure to a toxin or infectious agent.

9. The composition of claim 1, further wherein the composition is administered after exposure to a toxin or infectious agent.

10. The composition of claim 1, further comprising at least one adjuvant selected from the group consisting of aluminum salts, water-in-oil emulsions, oil-in-water emulsions, self-assembling macrostructures, cytokines, saponins, toll-like receptor agonists, immunostimulatory double stranded RNA species, unmethylated DNA oligonucleotides, and polymeric microparticles and nanostructures.

11. The composition of claim 1, further comprising at least one adjuvant comprising bacterial DNA and another adjuvant comprising flagellin.

12. The composition of claim 1, further comprising monophosphoryl lipid A.

13. The composition of claim 1, further comprising a co-adjuvant system consisting essentially of an aluminum salt, monophosphoryl lipid A, QS-21 and CpG sequences.

14. The composition of claim 1, wherein the first antigen is derived from ricin toxin and the second antigen is derived from *Bacillus anthracis*.

15. The composition of claim 14, wherein the first antigen derived from ricin toxin consists of a purified ricin A chain.

16. The composition of claim 14, wherein the second antigen derived from *Bacillus anthracis* consists of protective antigen (PA).

* * * * *

UNITED STATES PATENT AND TRADEMARK OFFICE

CERTIFICATE OF CORRECTION

PATENT NO. : 10,293,041 B2
APPLICATION NO. : 14/795872
DATED : May 21, 2019
INVENTOR(S) : Brey et al.

It is certified that error appears in the above-identified patent and that said Letters Patent is hereby corrected as shown below:

In the Specification

Column 7, Line 13: the word "vaccinees" should read "vaccines";

Column 26, Line 51: the word "Aihydrogel®" should read "Alhydrogel®";

Column 26, Line 61: the word "Aihydrogel®" should read "Alhydrogel®".

Signed and Sealed this
Sixteenth Day of July, 2019

Andrei Iancu
*Director of the United States Patent and Trademark Office*